(12) United States Patent
Nishinou et al.

(10) Patent No.: US 8,939,640 B2
(45) Date of Patent: Jan. 27, 2015

(54) RADIOGRAPHIC IMAGING DEVICE

(75) Inventors: Naoyuki Nishinou, Tokyo (JP); Haruyasu Nakatsugawa, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 305 days.

(21) Appl. No.: 13/636,698

(22) PCT Filed: Mar. 24, 2011

(86) PCT No.: PCT/JP2011/057259
§ 371 (c)(1),
(2), (4) Date: Sep. 24, 2012

(87) PCT Pub. No.: WO2011/125528
PCT Pub. Date: Oct. 13, 2011

(65) Prior Publication Data
US 2013/0010930 A1 Jan. 10, 2013

(30) Foreign Application Priority Data

Mar. 31, 2010 (JP) .................................. 2010-084581
Nov. 18, 2010 (JP) .................................. 2010-258225

(51) Int. Cl.
*H01J 31/49* (2006.01)
*A61B 6/00* (2006.01)

(52) U.S. Cl.
CPC .............. *A61B 6/4283* (2013.01); *A61B 6/4233* (2013.01); *A61B 6/547* (2013.01); *A61B 6/4452* (2013.01); *A61B 6/548* (2013.01)
USPC .... 378/189; 250/358.1; 250/366; 250/370.09

(58) Field of Classification Search
CPC .... G03B 42/04; A61B 6/4208; A61B 6/4405; A61B 2560/0431; G01T 1/2014; G01T 7/00

USPC ................... 378/189; 250/358.1, 366, 370.09
See application file for complete search history.

(56) References Cited

U.S. PATENT DOCUMENTS

| 2009/0134336 A1 | 5/2009 | Takahashi |
| 2009/0194700 A1* | 8/2009 | Kito et al. ................. 250/361 R |
| 2010/0078565 A1* | 4/2010 | Tsubota et al. ............ 250/358.1 |

FOREIGN PATENT DOCUMENTS

| JP | 62-52537 A | 3/1987 |
| JP | 62052537 | * 3/1987 |

(Continued)

OTHER PUBLICATIONS

Japanese Office Action dated Aug. 5, 2014, issued in corresponding Japanese Patent Application.

(Continued)

*Primary Examiner* — Michael Maskell
(74) *Attorney, Agent, or Firm* — SOLARIS Intellectual Property Group, PLLC

(57) ABSTRACT

An electronic cassette that is equipped with a drive mechanism capable of accommodating a radiation detection section respectively in two casings and that is capable of changing the surface area of the radiation detection section to be externally exposed and the exposure position on the radiation detection section. Deterioration of the radiation detection section from radiation can be distributed due to control such that the same exposure position is not repeatedly employed. An electronic cassette is accordingly provided that does not suffer from uneven effects of deterioration from radiation within a single sheet radiation detection section even with repeated use.

28 Claims, 22 Drawing Sheets

(56) References Cited

FOREIGN PATENT DOCUMENTS

| | | |
|---|---|---|
| JP | 1-140139 A | 6/1989 |
| JP | 2009-130209 A | 6/2009 |
| JP | 2009-205155 A | 9/2009 |
| JP | 2009-212389 A | 9/2009 |
| JP | 2010-6794 A | 1/2010 |
| JP | 2010-75439 A | 4/2010 |

OTHER PUBLICATIONS

International Search Report issued in International Application No. PCT/JP2011/057259 on Jun. 7, 2011.
Written Opinion of the ISA issued in International Application No. PCT/JP2011/057259 on Jun. 7, 2011.
Chinese Office Action dated May 20, 2014, issued in corresponding Chinese Patent Application.

* cited by examiner

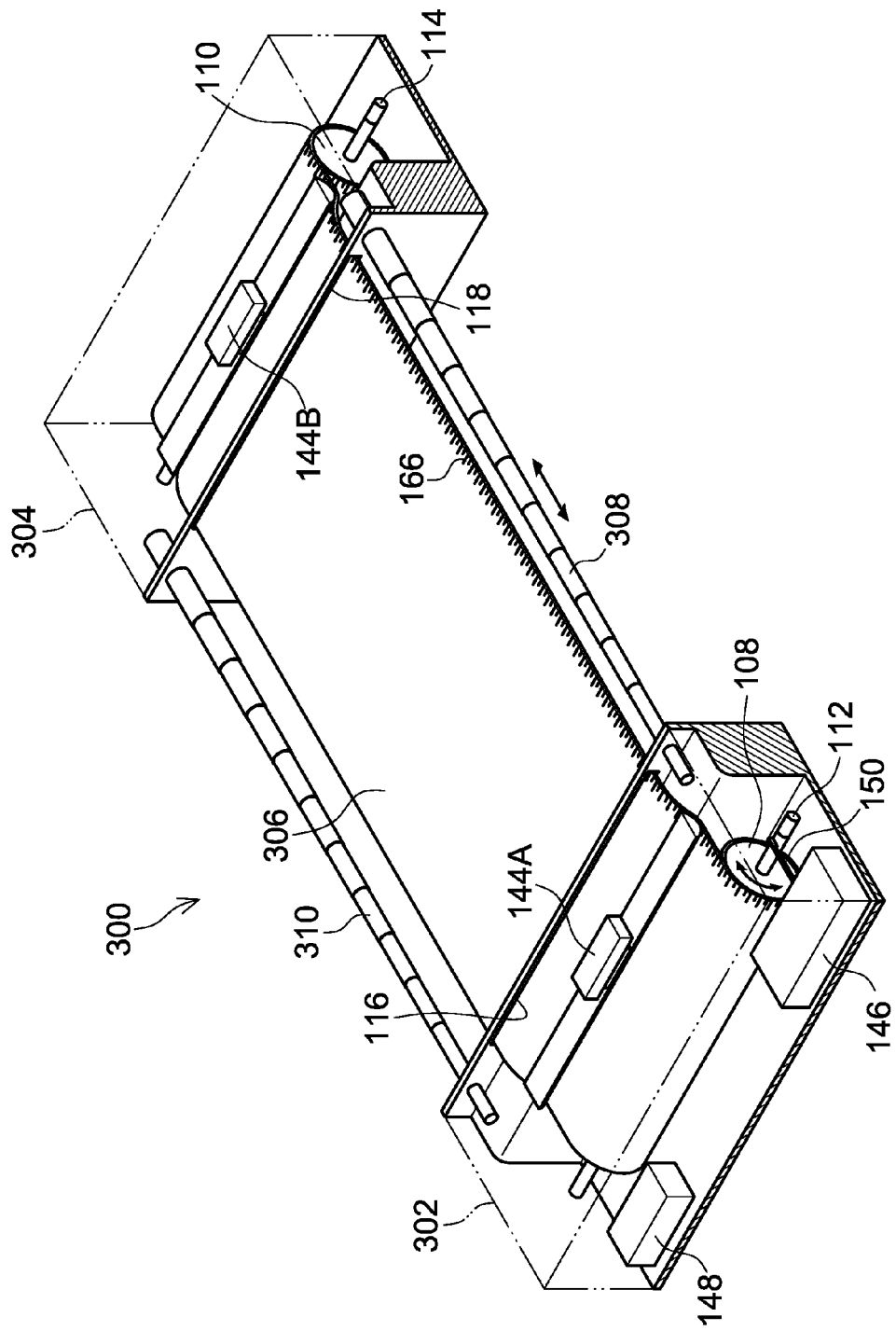

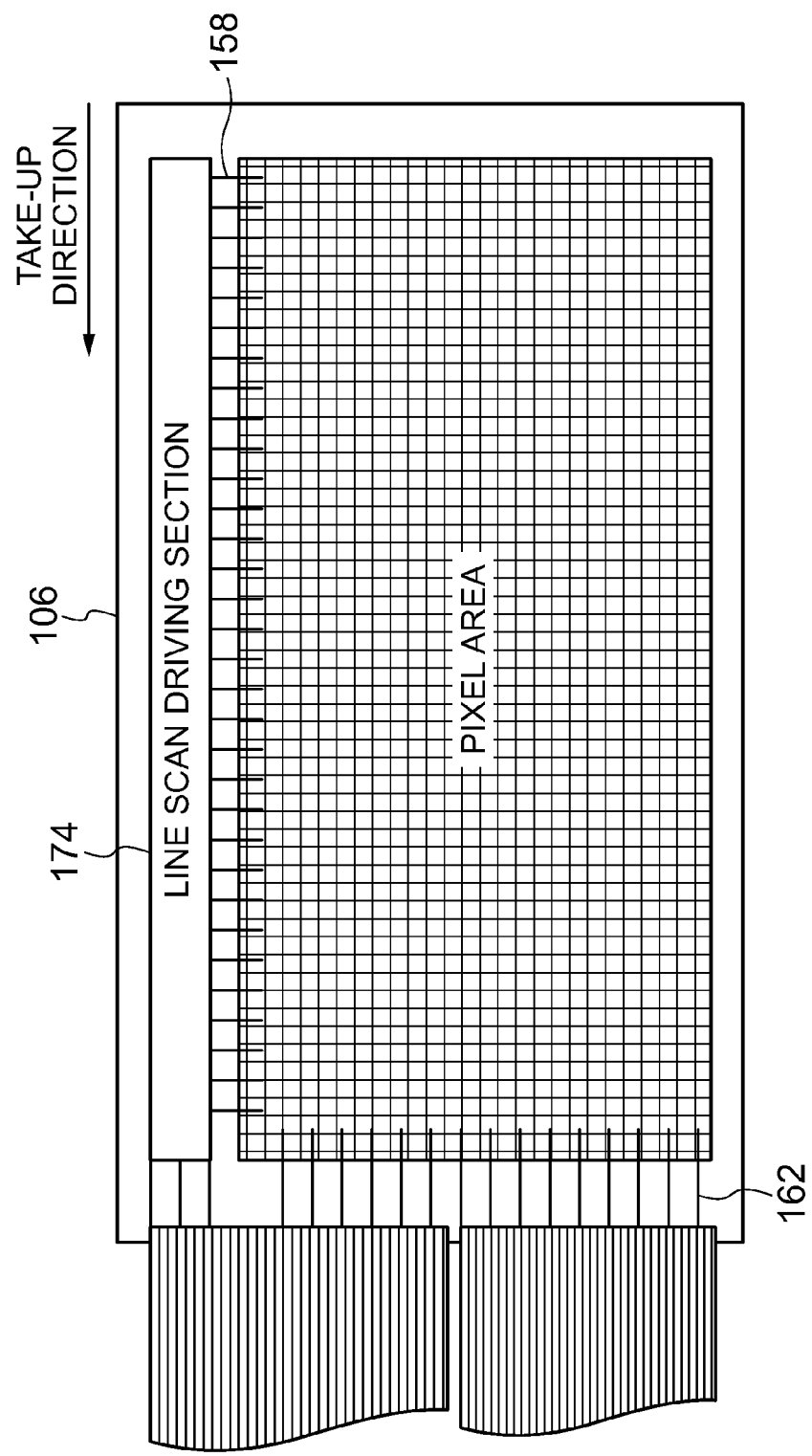

RADIOGRAPHIC IMAGING DEVICE

TECHNICAL FIELD

The present invention relates to a radiographic imaging device, and relates in particular to a radiographic imaging device provided with a flexible radiation detection section.

BACKGROUND ART

In radiographic imaging for medical diagnostics, a radiographic image detection apparatus is known that employs a radiographic imaging device (referred to below as an electronic cassette) to detect radiation that has passed through an imaging subject, and to convert the radiation into an electrical signal. Electronic cassettes include those employing a direct conversion method to convert radiation directly to an electrical signal by storing charge, and those that employ an indirect conversion method wherein radiation is first converted into visible light by a scintillator, and the visible light is then converted by solid state detection elements into an electrical signal by storing charge. Electronic cassettes have the advantage that radiographic images can be displayed immediately after imaging, and are becoming widely used.

Imaging has hitherto been performed employing films or electronic cassettes of varying sizes depending on the imaging site and imaging procedure. However, sometimes it is difficult to acquire plural electronic cassettes of varying sizes due to the high cost of electronic cassettes. In order to address this issue, electronic cassettes have recently been proposed in which the imaging surface area can be adjusted to match the imaging site by employing a single sheet flexible base, such as in Japanese Patent Application Laid-Open (JP-A) No. 2009-205155

DISCLOSURE OF INVENTION

Technical Problem

Electronic cassettes can be used repeatedly, however they suffer deterioration each time they are used due to being exposed to radiation. Specifically, as deterioration in the characteristics of semiconductors proceeds with radiation, concern arises, for example, regarding deterioration of the detection sensitivity of detectors and regarding deterioration of the switching characteristics of switching elements. In particular, in the electronic cassette of JP-A No. 2009-205155, the region of a radiation detection section close to the feedout opening is used many times, resulting in differences in deterioration condition arising between different regions even within a single sheet radiation detection section. When differences arise in deterioration condition between different regions of a single sheet radiation detection section, there is concern regarding, for example, differences in image quality when an imaging subject is a size requiring the radiation detection section to be fed out to its fullest extent. In consideration of the above circumstances, an object of the present invention is to provide an electronic cassette wherein the size and region used of a radiation detection section can be changed, and that can be used for a long time without deterioration of the radiation detection section due to repeated use being concentrated on one region.

Solution to Problem

A radiographic imaging device according to the present invention includes a flexible radiation detection section, a first casing, a second casing, a first drive mechanism that accommodates the radiation detection section inside the first casing and/or feeds out the radiation detection section from inside the first casing, and a second drive mechanism that accommodates the radiation detection section inside the second casing and/or feeds out the radiation detection section from inside the second casing. A portion at a first end of the radiation detection section is attached to the first drive mechanism, and a portion at a second end of the radiation detection section is attached to the second drive mechanism.

Another aspect includes an automatic drive mechanism that is provided at at least one of the first casing or the second casing and that automatically drives the first drive mechanism and/or the second drive mechanism, and a controller that controls the automatic drive mechanism.

Another aspect includes a position detection section that detects the position of the first casing and/or the position of the second casing with respect to the radiation detection section.

Advantageous Effects of Invention

According to the present invention, an electronic cassette is provided that can be used to provide high image quality over a long period of time.

BRIEF DESCRIPTION OF DRAWINGS

FIG. 14 is a perspective view of an electronic cassette according to a second exemplary embodiment.

FIG. 24 is a plan view illustrating a configuration of radiation detection section formed with a drive circuit.

BEST MODE FOR CARRYING OUT THE INVENTION

First Exemplary Embodiment

Figure 1:
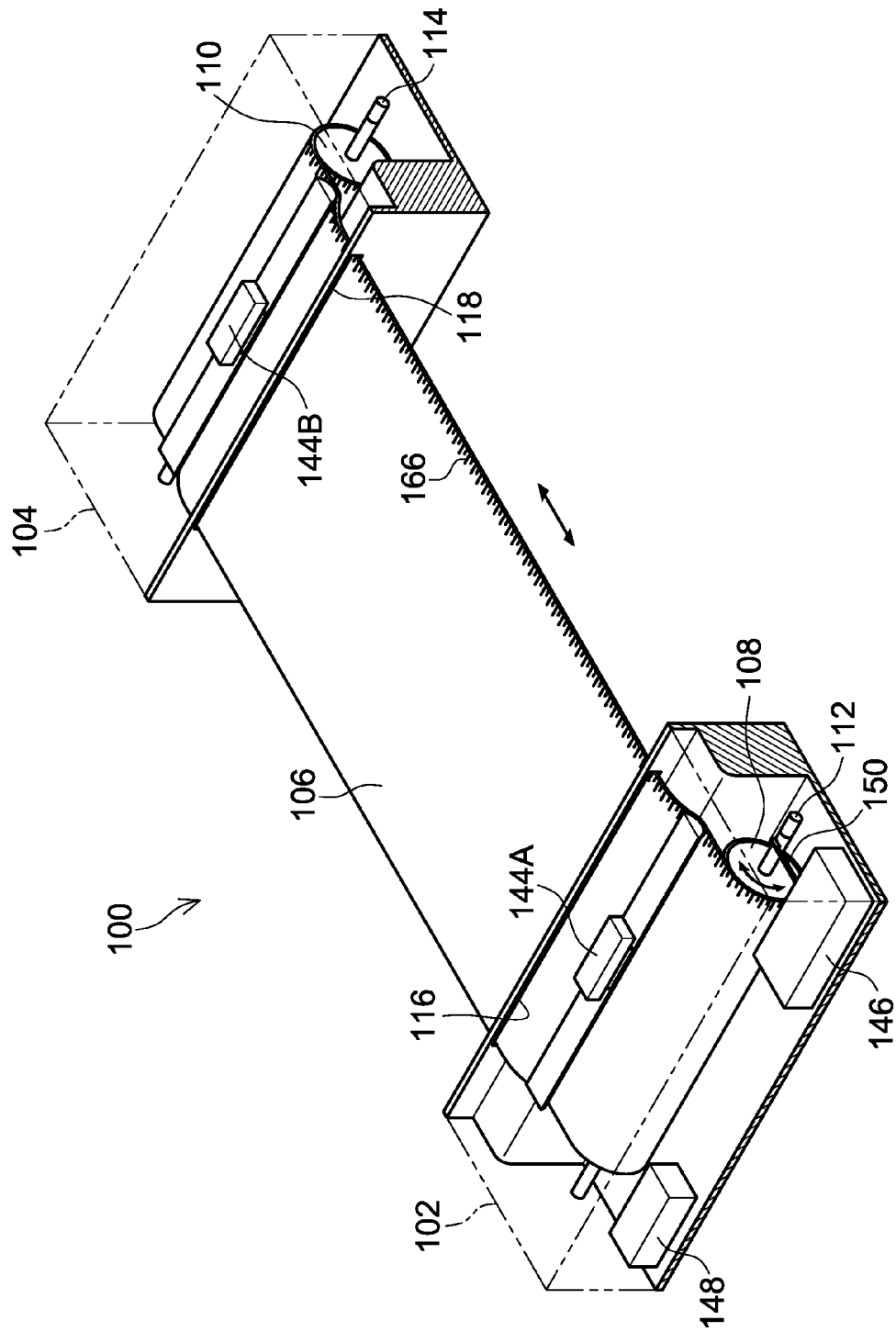
FIG. 1 is perspective view illustrating an electronic cassette according to a first exemplary embodiment.

FIG. 1 is an external perspective view of an electronic cassette 100 according to the present exemplary embodiment. Explanation follows regarding an outline configuration of the electronic cassette 100, with reference to FIG. 1. The cross-section of the casing is illustrated in FIG. 1 by hatching. The electronic cassette 100 includes a casing 102 and a casing 104 having substantially rectangular external shaped shapes, and a flexible radiation detection section 106 that can be accommodated inside the casing 102 or the casing 104, detects radiation from a radiation source that has passed through an imaging subject and coverts the radiation into radiographic image data. The radiation detection section 106 is formed in a rectangular sheet shape with a length sufficient for plural times of imaging by changing the imaging position. The radiation detection section 106, more specifically, has a long side of about 5 meters and a short side of about 1 meter.

In the casing 102 there is a circular column shaped take-up section 108 provided rotatably housed inside the casing 102. A rotation shaft 112 is provided inside the take-up section 108, running along the central axis of the take-up section 108. The rotation shaft 112 is longer than the central axis of the take-up section 108. The two ends of the rotation shaft 112 are exposed from the top face and the bottom face of the circular column shaped take-up section 108, and are rotatably attached to the inside wall of the casing 102. Due to such a configuration, the take-up section 108 rotates about an axis of the rotation shaft 112. In the casing 104 there is a circular column shaped take-up section 110 provided rotatably housed inside the casing 104. A rotation shaft 114 is provided inside the take-up section 110 running along the central axis of the take-up section 110. The configuration of the take-up section 110 and the rotation shaft 114 is similar to that of the take-up section 108 and the rotation shaft 112. The take-up section 110 accordingly rotates about an axis of the rotation shaft 114. The casing 102 has an opening portion 116 and the casing 104 has an opening portion 118. One end of the radiation detection section 106 passes through the opening portion 116 and the take-up section 108 and is fixed to the rotation shaft 112. A portion at the other end of the radiation detection section 106 passes through the opening portion 118 and the take-up section 110 and is fixed to the rotation shaft 114. Due to such a configuration, the electronic cassette 100 is capable of accommodating the radiation detection section 106 in the casing 102 or the casing 104 by winding the radiation detection section 106 onto the take-up section 108 or the take-up section 110. Such a configuration enables the surface area of the radiation detection section 106 that is external exposed (referred to below as the exposure surface area) to be varied within the range of the surface area of the radiation detection section 106, and enables the position of the region to be exposed (referred to below as the exposure position) out of the whole of the radiation detection section 106 to also be changed. The region of the radiation detection section 106 to be employed for imaging can be freely determined by a user. However, the two end portions of the radiation detection section 106, more specifically the two end portions of the region from the opening portion 116 to the rotation shaft 112 and the region from the opening portion 118 to the rotation shaft 114, cannot be exposed from either the casing 102 or the casing 104. A scale 166 is applied to the surface of the radiation detection section 106. The fed out amount of the radiation detection section 106 can accordingly be visibly discerned.

Figure 2:
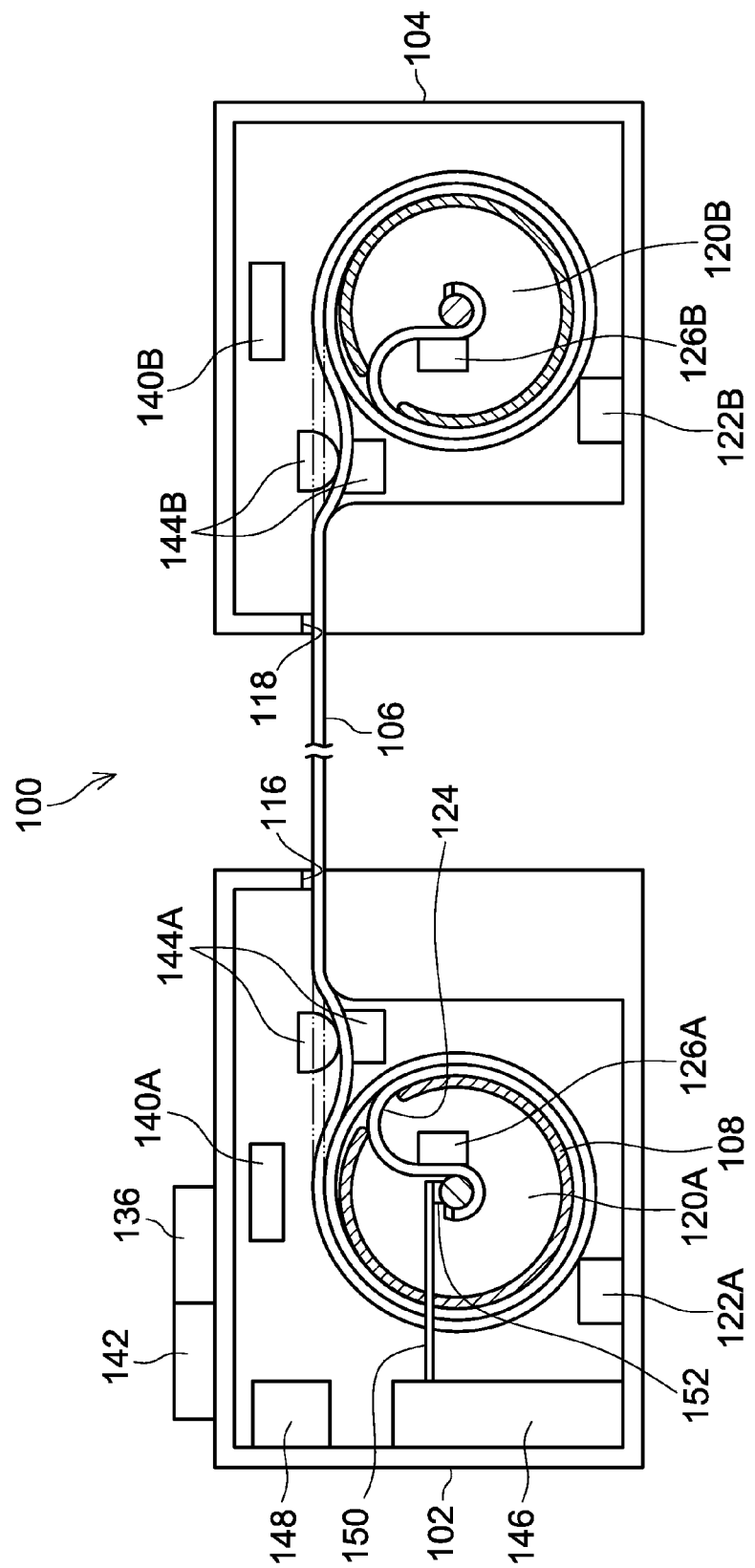
FIG. 2 is cross-section illustrating an electronic cassette according to the first exemplary embodiment.

FIG. 2 is a cross-section of the casing 102. Detailed explanation follows regarding configuration of the casing 102, with reference to FIG. 2. The casing 102 includes the circular column shaped take-up section 108 with internal hollow section 120, the rotation shaft 112 that passes through the take-up section 108 along the central axis of the take-up section 108, and a spring, not shown in the drawings, that is attached to the rotation shaft 112. The rotation shaft 112 is connected to the take-up section 108 through a circular shaped member, not shown in the drawings, provided to the top face and the bottom face of the circular column shaped take-up section 108. The two ends of the rotation shaft 112 are rotatably attached to the inner wall of the casing 102 through bearings. Due to such a configuration, the take-up section 108 is provided with an internal hollow space and also rotates about an axis of the rotation shaft 112. A motor 122A to control rotation of the rotation shaft is attached to the rotation shaft 112. The rotation shaft 112 is rotated by rotating the motor 122A, rotationally driving the take-up section 108. The take-up section 108 includes an opening portion 124 running along the length direction. The radiation detection section 106 passes through the opening portion 124, is accommodated in the hollow section 120 within the take-up section 108 and is wound on and fixed to the rotation shaft 112.

An electrical circuit 126A is mounted to a first end portion 106A of the radiation detection section 106. The electrical circuit 126A is accommodated inside the hollow section 120. A display section 142 and an input section 136 are also provided on the casing 102, and a take-up amount detection sensor 140A that detects the take-up amount of the radiation detection section 106 is also provided inside the casing 102. The input section 136 receives from a user such inputs as a radiation detection section 106 take-up command, a radiation detection section 106 feed-out command, patient data input, imaging site specification, and input operation of the surface area to be exposed of the radiation detection section 106. A known sensor can be employed for the take-up amount detection sensor 140A. A sensor that detects the number of rotations of the take-up section 108 is employed in the current case. The take-up amount detection sensor 140A computes the fed out amount of the radiation detection section 106 from the radial length of the take-up section 108 and the rotation angle of the take-up section 108, and outputs the computed amount to the display section 142. The display section 142 receives the output from the take-up amount detection sensor 140A and displays the exposed surface area of the radiation detection section 106. A stopper 144A is also provided in the vicinity of the opening portion 116 of the casing 102 for controlling the fed out amount of the radiation detection section 106. The stopper 144A nips the top face and the bottom face of the radiation detection section 106 to disable take-up and feed-out. The stopper 144A is capable of switching between an OFF state, in which take-up and feed-out of the radiation detection section 106 is enabled, and an ON state, in which take-up and feed-out of the radiation detection section 106 is disabled.

A detachable battery 146 and an input-output interface 148 are housed inside the casing 102. The battery 146 includes an external terminal 150 that extends to one end of the rotation shaft 112, and a brush 152 that is provided to the leading end of the external terminal 150 is in continuous contact with the rotation shaft 112. The brush 152, the rotation shaft 112, the radiation detection section 106, the electrical circuit 126A, the motor 122A, the input section 136, the take-up amount detection sensor 140A, the display section 142 and the stopper 144A are connected together electrically. Power from the battery 146 is supplied to the radiation detection section 106, the electrical circuit 126A, the motor 122A, the input section 136, the take-up amount detection sensor 140A, the display section 142 and the stopper 144A through the brush 152 and the rotation shaft 112.

A lead or copper plate, not shown in the drawings, is disposed at the inner wall of the casing 102. Damage to the casing 102 from irradiation of radiation, such as to the radiation detection section 106 and the electrical circuit 126A accommodated in the casing 102, is prevented by the lead plate.

The configuration of the casing 104 is substantially the same as that of the casing 102. A motor 122B, an electrical circuit 126B, a take-up amount detection sensor 140B and a stopper 144B in the casing 104 are electrically connected through the radiation detection section 106 to the electrical circuit 126A and the battery 146. Such a configuration enables the battery 146 in the casing 102 to act as a power source for inside the casing 104, eliminating the need to provide a battery inside the casing 104.

Figure 3:
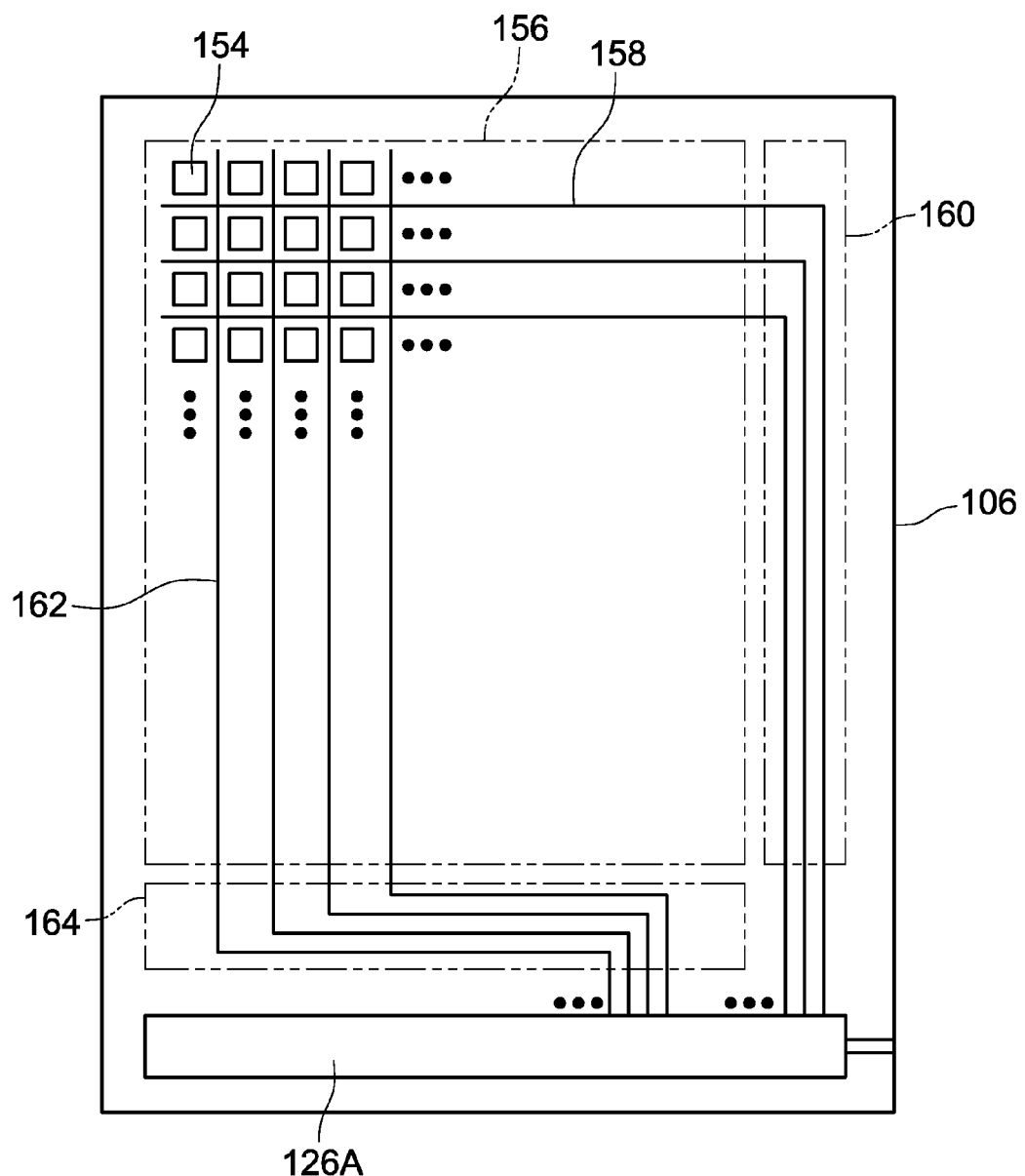
FIG. 3 is a plan view illustrating a radiation detection section.

FIG. 3 is a plan view of the radiation detection section 106. Explanation follows regarding configuration of the radiation detection section 106, with reference to FIG. 3. The radiation detection section 106 is flexible. More specifically, the radiation detection section 106 includes a radiation conversion section 156 formed with a great number of pixels 154, a first flexible wiring section 160 formed with a great number of gate lines 158 leading to the great number of pixels 154, and a second flexible wiring section 164 formed with a great number of signal lines 162 leading to the great number of pixels 154.

Figure 4:
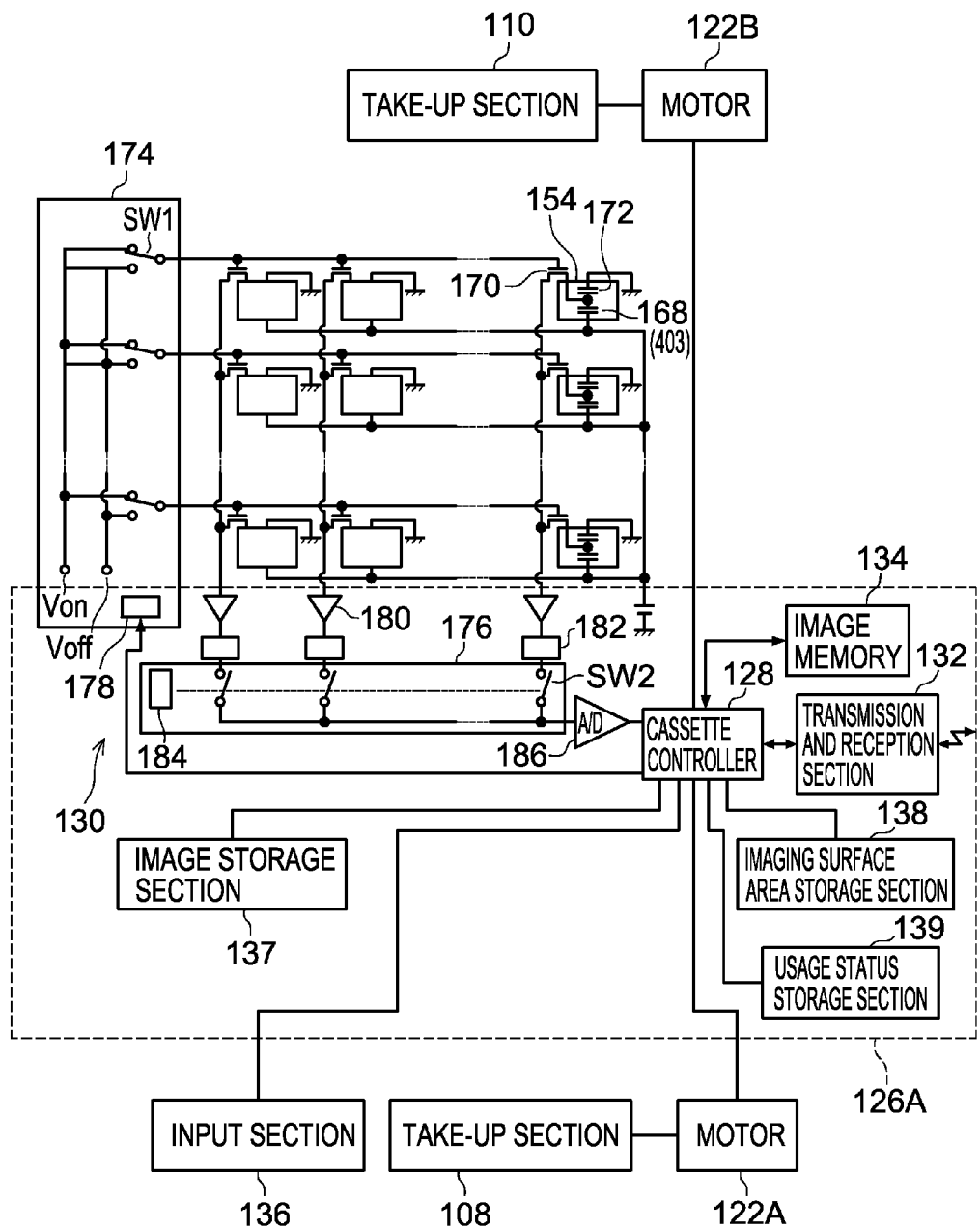
FIG. 4 is a block diagram of a circuit configuration of an electronic cassette.

FIG. 4 is a block diagram of a circuit configuration of the radiation detection section 106 and peripheral configuration thereto. Explanation follows regarding details of the configuration of the radiation detection section 106, with reference to FIG. 4. An end portion of the radiation detection section 106 includes the electrical circuit 126A. The electrical circuit 126A includes a cassette controller 128, a readout circuit 130, a transmission and reception section 132, an image memory 134, the input section 136, an image storage section 137, an imaging surface area storage section 138 and a usage status storage section 139.

The cassette controller 128 controls driving of the circuits of the radiation detection section 106, driving of the electrical circuit 126A, driving of the circuit drive electrical circuit 126B, driving of the motor 122A, driving of the motor 122B, ON/OFF control of the stopper 144A, and ON/OFF control of the stopper 144B. The readout circuit 130 reads radiographic image data converted by the radiation detection section 106.

The transmission and reception section 132 transmits and receives signals including the radiographic image data read by the readout circuit 130. The image memory 134 stores the radiographic image data read by the readout circuit 130. The image storage section 137 is a read-write capable memory. The image storage section 137 is stored with data such as captured radiographic images and data relating to the imaged patient. The imaging surface area storage section 138 is stored with the operation program of the electronic cassette 100 and values of exposure surface area of the radiation detection section 106 corresponding to each imaging site specified by the input section 136. The usage status storage section 139 is stored with the usage status of the radiation detection section 106. More specifically, the usage status storage section 139 is stored with the region of the radiation detection section 106 employed for imaging the previous time, and the number of respective imaging times for each of plural regions into which the radiation detection section 106 is partitioned. The cassette controller 128 performs control based on the usage status of the radiation detection section 106 stored in the usage status storage section 139 such that the same region is not repeatedly employed for imaging. Uneven deterioration of a particular region of the radiation detection section 106 is thereby avoided. Known storage devices, such as hard disk(s), can be employed for the image storage section 137, the imaging surface area storage section 138 and the usage status storage section 139. The input-output interface 148 transmits and receives signals including radiographic image data with the transmission and reception section 132. Exchange of signals between the transmission and reception section 132 and the input-output interface 148 can be performed by radio waves at a frequency of 3 kHz to 3T (Tera) Hz, or by infrared radiation. When performed by radio waves, signal exchange can be implemented by providing respective transmission and reception antennae in the transmission and reception section 132 and the input-output interface 148.

Photoelectric conversion layers 168 are formed from a substance that is sensitive to radiation and generates charge, such as amorphous selenium (a-Se). The photoelectric conversion layers 168 are disposed over an array of Thin Film Transistors (TFTs) 170 arrayed in rows and columns. In the photoelectric conversion layers 168, after generated charges have been accumulated in storage capacitors 172, the TFTs 170 are then switched ON, sequentially by row, through the gate lines 158, and the charges are read out as image signals. FIG. 4 illustrates details of only the connection relationships between a single of the pixels 154, formed by the photoelectric conversion layer 168 and the storage capacitor 172, and a single of the TFTs 170, with the configuration of other pixels omitted in the drawing. The gate lines 158 that extend parallel to the row direction and the signal lines 162 that extend parallel to the column direction are connected to the respective TFTs 170 connected to each of the pixels 154. Each of the gate lines 158 is connected through the first flexible wiring section 160 to a line scan drive section 174 of the readout circuit 130. Each of the signal lines 162 is connected through the second flexible wiring section 164 to a multiplexer 176 of the readout circuit 130. The gate lines 158 are supplied with control signals Von, Voff from the line scan drive section 174 for ON/OFF controlling the TFTs 170 that are arrayed along a row direction. The line scan drive section 174 is equipped with plural switches SW1 for switching the gate lines 158 and a first address coder 178 that outputs a selection signal for selecting one switch SW1 out of the switches SW1. An address signal is supplied from the cassette controller 128 to the first address coder 178. Charges held in the storage capacitor 172 of each of the pixels 154 flows out through the TFTs 170 arrayed in a column direction to the signal lines 162. The charges are amplified by amplifiers 180 of the readout circuit 130. The multiplexer 176 is connected to the amplifiers 180 through sample and hold circuits 182 of the readout circuit 130. The multiplexer 176 is equipped with plural switches SW2 for switching the signal lines 162 and a second address coder 184 that outputs a selection signal for to select one switch SW2 out of the plural switches SW2. The second address coder 184 is supplied with an address signal from the cassette controller 128. An A/D converter 186 of the readout circuit 130 is connected to the multiplexer 176. Radiographic image data is converted into a digital signal by the A/D converter 186 and stored through the cassette controller 128 in the image memory 134. The radiographic image data stored in the image memory 134 is transmitted through the transmission and reception section 132 and the input-output interface 148 to a portable data terminal, not shown in the drawings. The radiographic image data can also be stored in the image storage section 137. The radiographic image data is subjected to data compression as required.

Figure 5:
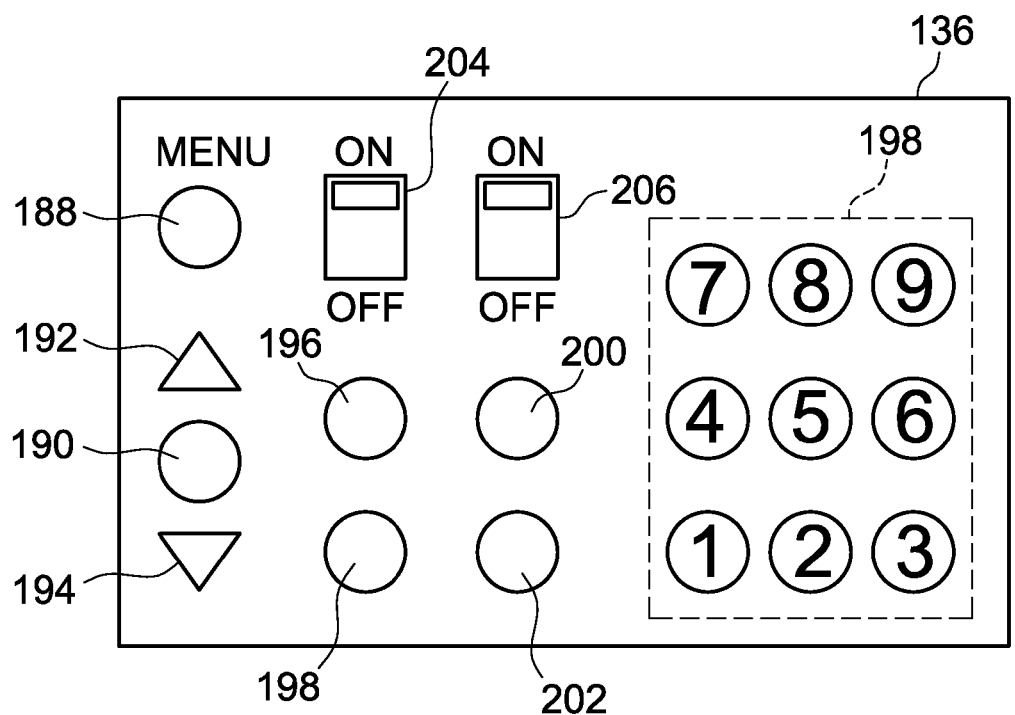
FIG. 5 is a schematic drawing of an input section.

Explanation follows regarding each of the buttons of the input section 136, with reference to FIG. 5. FIG. 5 is a schematic diagram of the input section 136. The input section includes a menu button 188, an enter button 190, an UP button 192, a DOWN button 194, a take-up button 196 for taking up the radiation detection section 106 in the casing 102, a feed-out button 198 for feeding out the radiation detection section 106 from the casing 102, a take-up button 200 for taking up the radiation detection section 106 in the casing 104, a feed-out button 202 for feeding out the radiation detection section 106 from the casing 104, an ON/OFF switch 204 for the stopper 144A of the casing 102, and an ON/OFF switch 206 for the stopper 144B of the casing 104.

The power of the electronic cassette 100 is switched ON when a user presses the menu button 188 for a specific duration. The menu button 188 is a button for displaying an imaging menu. The imaging menu is displayed on the display section 142 when the menu button 188 is pressed. The imaging menu includes modes such as a specification mode for specifying the imaging surface area based on imaging site, a direct specification mode for the imaging surface area, a specification mode for specifying imaging surface area from a displayed map, and an input mode for patient data. Selection on the imaging menu is performed with the UP button 192, the DOWN button 194 and the enter button 190.

In the imaging site specification mode a user is able to specify the site for imaging from out of, for example, sites such as the chest, head, abdominal region, arm or leg. When the imaging site has been specified, the cassette controller 128 reads out the imaging surface area corresponding to each of the sites that has been pre-stored in the imaging surface area storage section 138. In the direct specification mode a user is able to input numerical values using a ten-key 198 to input the surface area.

The direct specification mode for the imaging surface area is employed in cases when it is desired to select an imaging surface area of a size of that cannot be selected by correspondence to a specified region alone. In the specification mode by imaging surface area display map, the exposure surface area and the exposure position are manually adjusted from a map displayed on the display section 142 of all regions of the radiation detection section 106, the exposure surface area and the exposure position.

A user can freely specify the exposure surface area and the exposure position of the radiation detection section 106 in the specification mode by imaging surface area display map. A user can input patient data using the ten-key 198 in the patient data input mode.

Take-up or feed-out of the radiation detection section 106 to or from the casing 102 or the casing 104 can be instructed by the take-up button 196 for taking up the radiation detection section 106 in the casing 102, the feed-out button 198 for feeding out the radiation detection section 106 from the casing 102, the take-up button 200 for taking up the radiation detection section 106 in the casing 104 and the feed-out button 202 for feeding out the radiation detection section 106 from the casing 104. The size of the exposure surface area can be adjusted by employing these buttons when for example a larger exposure surface area is desired or when a smaller exposure surface area is desired. The ON/OFF switch 204 for the stopper 144A of the casing 102 and the ON/OFF switch 206 for the stopper 144B of the casing 104 enable the stoppers 144A, 144B provided to the casing 102 and the casing 104 to be manually switched ON/OFF. The radiation detection section 106 can be manually fed-out from the casing 102 or the casing 104 by switching OFF the ON/OFF switch 204 or the ON/OFF switch 206.

Figure 6:
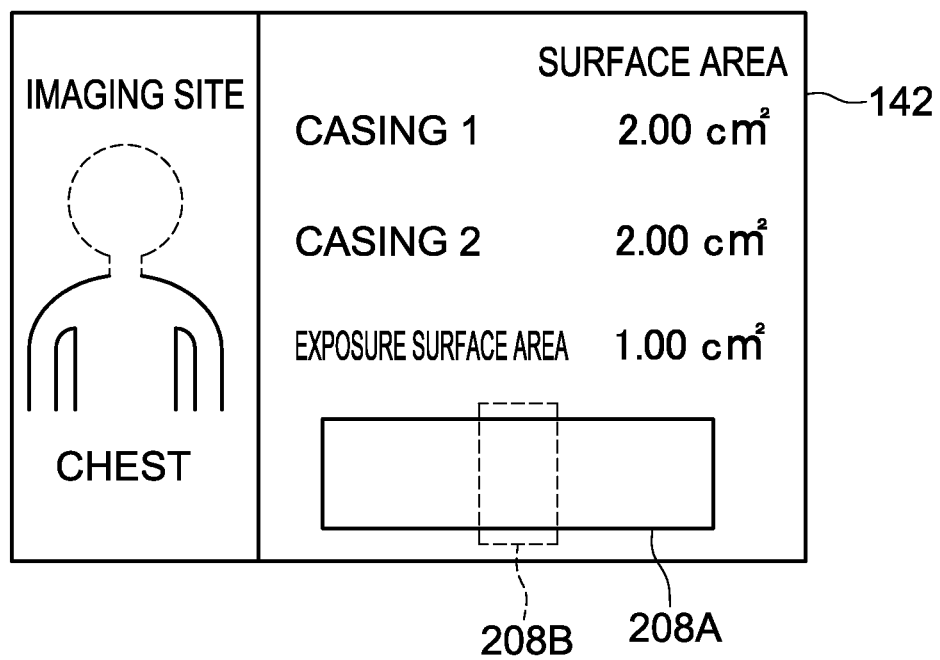
FIG. 6 is a schematic drawing of a display section.

FIG. 6 is an example of a display on the display section 142. The display section 142 displays the specified imaging site, the surface area of the radiation detection section 106 accommodated in the casing 102 and the casing 104, the total region 208A of the radiation detection section 106, the exposure surface area and exposure position 208B. In FIG. 6, numerical values of the surface area taken-up inside each of the casings are displayed on the display section 142. Display on the display section 142 can also be employed to display how many portions worth of surface area are wound on in relation to the imaging site, such as x portions of chest or y portions of leg. More specifically, whether a given number of portions worth of the surface area corresponding to each of the imaging sites are currently wound on can be computed by dividing the surface area taken-up inside each of the casings by the surface area corresponding to each site. A user can thereby easily directly ascertain the surface area taken-up inside each of the casings when displayed corresponding to each imaging site in this manner.

Explanation follows regarding operation of the electronic cassette 100.

When the electronic cassette 100 is not being used by a user the radiation detection section 106 is wound into the casing 102 or the casing 104, and the exposure surface area of the radiation detection section 106 is then held in the 0 state (referred to below as the accommodated state).

When the electronic cassette 100 is in use, a user switches the power ON and inputs patient data with the input section 136. More specifically, data such as the name and ID of the patient for investigation is input. The exposure surface area of the radiation detection section 106 is then set with the input section 136. For example, when the imaging site has been specified with the input section 136, the cassette controller 128 reads out the surface area corresponding to the specified imaging site from the imaging surface area storage section 138. The cassette controller 128 computes the angles the take-up section 110 and the take-up section 108 need to be rotated to, based on the exposure surface area corresponding to the imaging site read from the imaging surface area storage section 138, the surface area of the radiation detection section 106 that is wound on the take-up section 108, and the surface area of the radiation detection section 106 that is wound on the take-up section 110. Normally the exposure position of the radiation detection section 106 is changed by performing take-up or feed-out of the radiation detection section 106 in one of the feed-out directions. More specifically, the angle to rotate the take-up section 108 or the take-up section 110 is computed based on the exposure surface area corresponding to the imaging site and the length of the radius of the take-up section 108 or the take-up section 110. After completion of angle computation, the cassette controller 128 transmits a command to switch the stoppers OFF, and transmits a command to rotate the motors by the computed angle. When rotation of the motors is complete the cassette controller transmits a command to switch the stoppers ON, thereby disabling take-up or feed-out of the radiation detection section 106. The cassette controller 128 thus rotates the take-up section 108 to adjust such that the exposure surface area of the radiation detection section 106 is the same as the exposure surface area read from the imaging surface area storage section 138.

Figure 7:
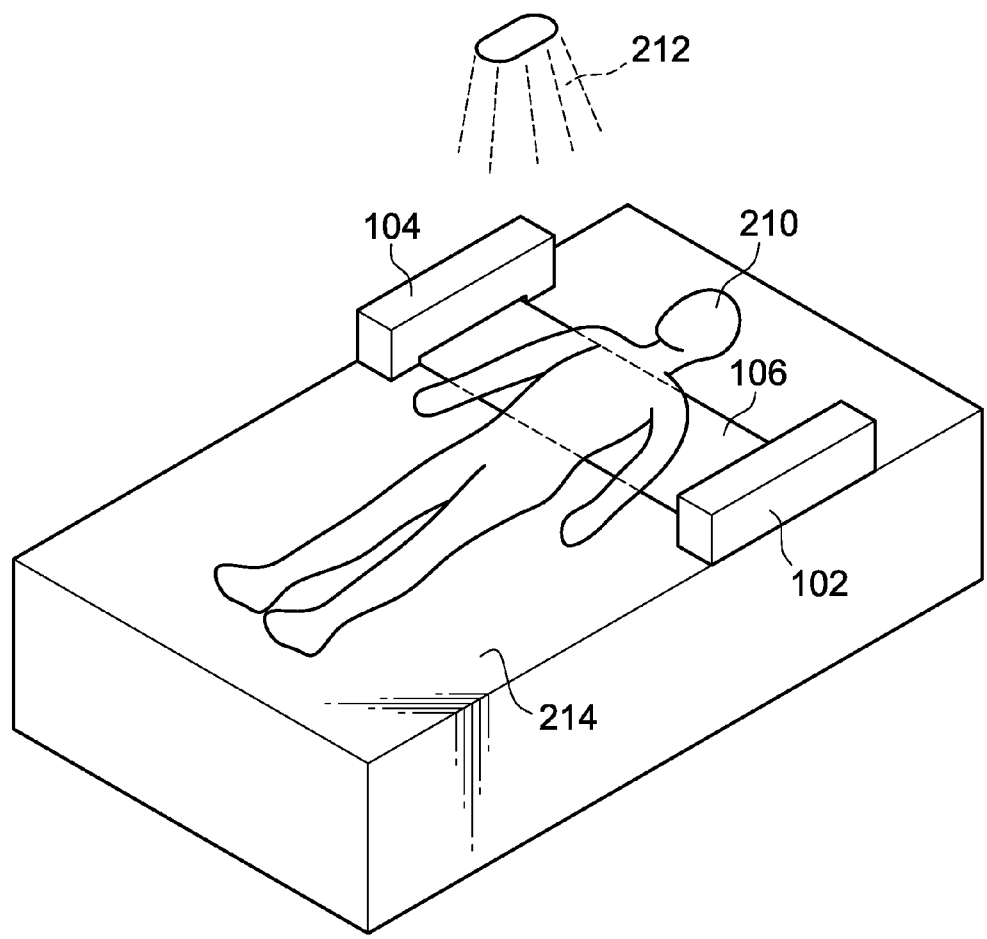
FIG. 7 is a usage example of an electronic cassette according to the first exemplary embodiment.

FIG. 7 is a schematic diagram during use of the electronic cassette 100. FIG. 7 illustrates a patient 210 lying on a bed 214 and represents a situation in which the chest of the patient 210 is being imaged. The electronic cassette 100 is placed between the patient 210 and the bed 214. More specifically, the electronic cassette 100 is placed such that the radiation detection section 106 is positioned between the chest of the patient 210 and the bed 214. Imaging is performed by irradiating radiation from a radiation irradiation section 212 above the patient, through the patient 210 and towards the radiation detection section 106.

The radiation that has passed through the patient 210 is converted into electrical signals by the photoelectric conversion layer 168 of each of the pixels 154 configuring the exposed radiation detection section 106, and the electrical signals are held as charges in the storage capacitors 172. The charge data, which is the radiographic image data of the patient 210 held in each of the storage capacitors 172, is then read according to address signals supplied from the cassette controller 128 to the line scan drive section 174 and the multiplexer 176.

The first address coder 178 of the line scan drive section 174 outputs a selection signal to select one of the switches SW1 according to the address signal supplied from the cassette controller 128, and supplies a control signal Von to the gate of the TFTs 170 connected to the corresponding gate line 158. The second address coder 184 of the multiplexer 118 outputs a selection signal according to the address signal supplied from the cassette controller 128 and successively switches the switches SW2. The radiographic image data that is the charge data held in the storage capacitor 172 of each of the pixels 154 connected to the gate line 158 selected by the line scan drive section 174 is then read out in sequence through the signal lines 162.

The radiographic image data read from the storage capacitor 172 of each of the pixels 154 connected to the selected gate line 158 is sampled by each of the sample and hold circuits 182 after being amplified by each of the amplifiers 180 and supplied to the A/D converter 186 through the multiplexer 176, where it is converted into a digital signal. The radiographic image data converted into a digital signal is temporarily stored in the image memory 134 of the cassette controller 128.

The first address coder 178 of the line scan drive section 174 switches the switches SW1 in sequence according to the address signal supplied from the cassette controller 128, and the radiographic image data that is the charge data held in the storage capacitor 172 of each of the pixels 154 connected to each of the gate lines 158 is read from the signal lines 162. The read radiographic image data is stored in the image memory 134 through the multiplexer 176 and the A/D converter 186 and the cassette controller 134. When the radiographic image data has been stored in the image memory 134, the cassette controller 128 identifies the position on the radiation detection section 106 that was employed for imaging. More specifically the exposure surface area and the exposure position of the radiation detection section 106 is identified from the values of the take-up amount detection sensors of the casing 102 and the casing 104. The cassette controller 128 stores the identified exposure surface area and exposure position in the usage status storage section 139.

The cassette controller 128 also stores the number of times of use for each of the exposure positions of the radiation detection section 106 in the usage status storage section 139. More specifically, the total region of the radiation detection section 106 is divided in the radiation detection section 106 feed-out direction into lcm units, and the region that was used is identified from the values of the take-up amount detection sensors of the casing 102 and the casing 104. The number of times of use for the identified regions is then incremented by 1 and stored. The number of times of use of the radiation detection section 106 can accordingly be stored by 1 cm units in the feed-out direction. After subjecting the radiographic image data stored in the image memory 134 to compression processing, the radiographic image data is stored in the image storage section 137 or transmitted to a portable data terminal by wireless communication through the transmission and reception section 132 and the input-output interface 148.

When follow-on imaging is to be performed, the cassette controller 128 controls rotation of the take-up section 108 and the take-up section 110 to expose a different region to the region employed for imaging immediately previously that is stored in the usage status storage section 139. In such cases, when the exposure surface area employed for imaging previously and the exposure surface area for employing in imaging the next time are the same as each other, the motor 122A and the motor 122B are rotationally driven at equivalent speeds to each other, and take-up or feed-out is performed by the amount of the surface area employed for imaging previously, such that only the exposure position is changed without altering the exposure surface area. When the exposure surface area employed for imaging previously and the exposure surface area to be employed in imaging the next time differ from each other, a difference is applied between the speeds or rotation times for rotationally driving the motor 122A and the motor 122B. For example, when the exposure surface area is to be made smaller than the exposure surface area employed for imaging previously, the cassette controller 128 controls to make the rotation amount of the motor on the feed-out side smaller than the rotation amount of the motor on the take-up side, or to switch ON the stopper on the feed-out side when the desired exposure surface area is reached.

After completing radiographic image capture, the take-up button 196 for taking up the radiation detection section 106 in the casing 102 or the take-up button 198 for taking up the radiation detection section 106 in the casing 104 is pressed by the user. According to operation of the take-up button 196 or the take-up button 198, the cassette controller 128 outputs an OFF command to the stoppers, and then outputs a take-up command to the motor inside the casing 102 or the casing 104, and winds the radiation detection section 106 into the take-up section 108 or the take-up section 110 to adopt the accommodated state.

In the electronic cassette 100 of the present exemplary embodiment the exposure surface area and the exposure position of the radiation detection section 106 are accordingly variable, and control is performed such that a different exposure position is employed to the exposure position immediately previous, thereby eliminating deterioration of the radiation detection section due to radiation being concentrated on the same region.

Figure 8:
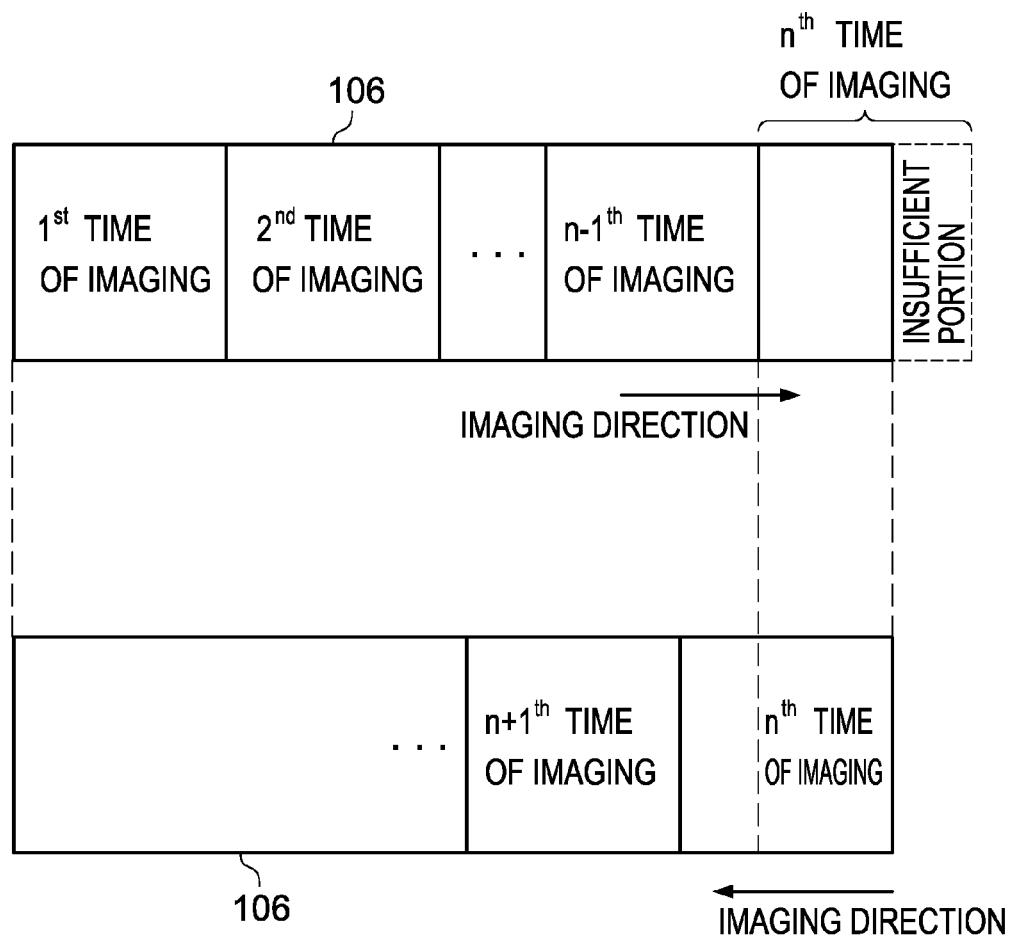
FIG. 8 is an example of control of how a radiation detection section is used in a first imaging direction, and an example of control of how the radiation detection section is used in a second imaging direction.

Explanation follows regarding an example of exposure position change operation of the radiation detection section 106 when imaging is performed plural times with the electronic cassette 100, with reference to FIG. 8. FIG. 8 is a diagram schematically depicting the radiation detection section 106. As explained above, each time imaging is performed the electronic cassette 100 stores in the usage status storage section 139 the exposure surface area and the exposure position of the radiation detection section 106 and the number of times of use for each exposure position, and imaging is completed. The electronic cassette 100 receives patient data and exposure surface area input operation from a user at each imaging completion.

The cassette controller 128 that has received the specified patient data and exposure surface area from the user, as shown in FIG. 8, employs the radiation detection section 106 that is initially wound only on one of the take-up sections (referred to as take-up section A) by feeding out the radiation detection section 106 in the feed-out direction. In such cases control is performed such that the region employed for imaging the previous time is not externally exposed during imaging the next time. When the surface area specified by the user is larger than the surface area still wound on the take-up section A (at the $n^{th}$ time in FIG. 8), the cassette controller 128 performs feed-out of the whole of the radiation detection section 106 from the take-up section A, performs take-up or feed-out of the other take-up section (take-up section B), and then performs control such that the exposure surface area of the radiation detection section 106 become the same as the specified exposure surface area (FIG. 8). In other words, the exposure surface area specified by the user is exposed by feeding out towards the take-up section A from a state in which the radiation detection section 106 is only wound on the take-up section B. By performing such control, even when the surface area is insufficient for use by feeding out in the same direction, the re-used range of the region employed immediately previously can be made narrower. Since the radiation detection section 106 is sequentially used from one end thereof, it is possible to accommodate cases in which different surface areas are desired each time of imaging, and the usage status of the radiation detection section 106 can be evened out.

According to the electronic cassette 100 of the first exemplary embodiment as described above, the exposure surface area and the exposure position of the radiation detection section 106 are variable since a configuration is adopted in which it is possible to accommodate the radiation detection section 106 in the casing 102 or the casing 104. The electronic cassette 100 stores the region of the radiation detection section 106 employed for imaging and controls such that a different exposure position is externally exposed to the exposure position employed immediately previously. Hence concentration of deterioration due to radiation in the same exposure position is eliminated. The electronic cassette 100 also takes up the radiation detection section 106 when not in use, achieving the accommodated state, and so the electronic cassette 100 can be put away in a compact state, achieving convenience in portability.

When, as in the present exemplary embodiment, a motor for automatically rotating the take-up sections is provided inside each of the casings, the exposure surface area and the exposure position of the radiation detection section 106 can be automatically adjusted. When placing the electronic cassette 100 in the accommodated state, rapid change to the accommodated state can be achieved by performing take-up with each of the two motors.

As in the present exemplary embodiment, when the radiation detection section 106 is configured in a rectangular sheet, the length of the short side is uniform, and so the surface area can be computed merely from the change in length in the take-up direction. The computation of surface area is thereby simplified and rotation of the motor can be easily controlled.

Figure 9:
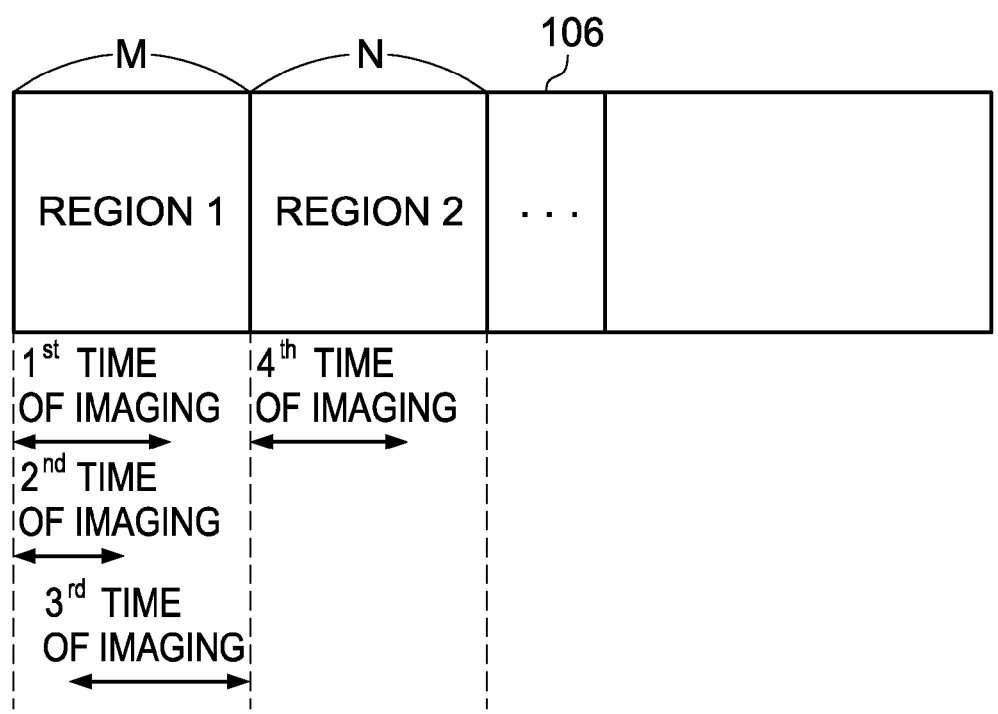
FIG. 9 is an example of control wherein the same region of a radiation detection section is used multiple times.

Explanation follows of another example of exposure position change operation of the radiation detection section 106 when imaging is performed plural times with the electronic cassette 100, with reference to FIG. 9. FIG. 9 is a diagram schematically depicting a radiation detection section. Imaging is performed plural times in this example with the same exposure position, and the exposure surface area and exposure position can be changed when imaging has been performed a preset number of times. More specifically, the cassette controller 128 controls the rotation of the take-up section 108 and the take-up section 110 and adjusts the exposure surface area and position to start by using the region 1 shown in FIG. 9, and switches the stoppers ON. The arrows in the diagram indicate the respective widths employed for imaging. For example, a user inputs the exposure surface area, and the cassette controller 128 rotates the take-up section 108 and the take-up section 110 such that the region 1 of width M corresponding to the input exposure surface area is externally exposed. Imaging is then performed 3 times in the region 1 irrespective of the width employed for imaging (indicated by the length of the arrows in the diagram). The cassette controller 128 then switches the stoppers OFF. This is succeeded by input of an exposure surface area from the user. The cassette controller 128 controls the rotation of the take-up section 108 and the take-up section 110 such that the region 2 of width N corresponding to the exposure surface area input by the user is externally exposed, and switches the stoppers ON. Imaging is then performed 3 times in region 2 and then region 3 is employed. This pattern is repeated, using one adjacent region in sequence for each 3 times of imaging. By continuing to employ the radiation detection section 106 in this manner, the need to adjust the width of the region for each time of imaging is eliminated while still employing the desired width in sequence from the end of the radiation detection section 106, enabling a reduction in power consumption to be achieved. Since the same region is repeatedly employed the specific number of times, the number of times of use can be made the same for each of the regions.

When it is desired to accommodate the electronic cassette 100 prior to using a predetermined number of times, to accommodate in a casing whose stopper is OFF, or to accommodate in a casing not provided with a stopper, control is performed to switch only one stopper ON in the electronic cassette 100, such that the currently employed position is not changed. Such control enables the accommodated state to be achieved without changing the exposure position of the radiation detection section 106. Therefore the accommodated state can be achieved while fixing to the region that was being employed, even in cases when sudden carrying or storage is required during imaging. Note that although an example has been given here of usage 3 times there is no limitation to 3 times.

There is also no limitation to changing the region based on the number of times of imaging. For example, a function may be provided for measuring the cumulative radiation dose at plural locations on the radiation detection section 106, and the region to be employed changed based on the cumulative radiation dose. When, in measuring the cumulative radiation dose, the same exposure position is employed a number of times and this exposure position has reached a preset radiation dose, a command is output from the cassette controller 128, and control is performed to switch the stoppers OFF such that the position of the radiation detection section 106 becomes variable. Such control enables the region of use to be changed when the cumulative radiation dose has reached a specific value, enabling usage such that the cumulative radiation dose of the whole of the radiation detection section 106 is substantially even. The cumulative radiation dose need not necessarily be measured by a function for detecting the cumulative radiation dose. For example, configuration may be made such that the cassette controller 128 performs communication with an X-ray source, and estimated values of the cumulative radiation dose associated with the exposure regions of the radiation detection section 106 are derived.

Figure 10:
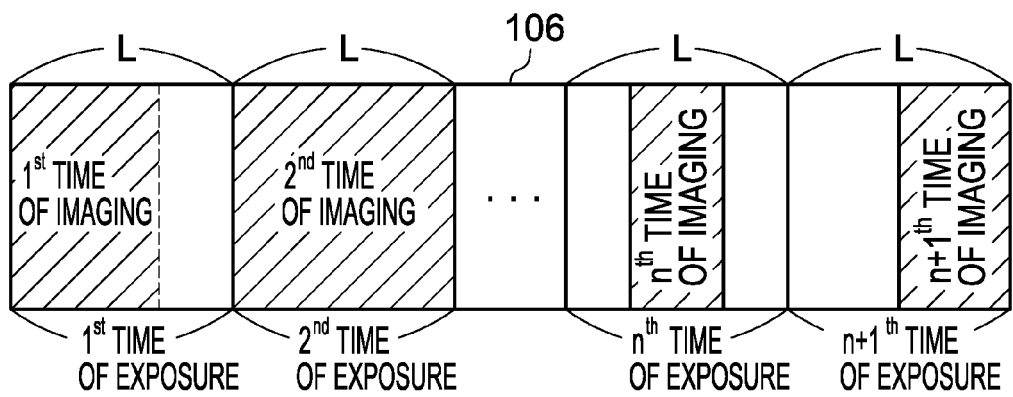
FIG. 10 is an example of control wherein the region of a radiation detection section used is different each time.

Explanation follows of another example of exposure position change operation of the radiation detection section 106 when imaging is performed plural times employing the electronic cassette 100, with reference to FIG. 10. FIG. 10 is a diagram schematically depicting a radiation detection section. The portions that are hatched and portions encircled by the dotted lines in FIG. 10 indicate the regions employed for imaging. In this example the radiation detection section 106 is evenly divided up at length L, and the exposure surface area for each time of imaging is made even. In this example, the region adjacent on the right is employed each time of imaging, irrespective of how much surface area has been employed for imaging each time. Starting by employing the region at the left end illustrated in FIG. 10, the portion for the first time of imaging surrounded by the hatching in FIG. 10 is employed for the first time of imaging. After imaging has been completed the first time, the cassette controller 128 drives the take-up section 108 and the take-up section 110 such that the preset region adjacent on the right is exposed. After the second time of imaging, similarly to after the first time of imaging, irrespective of whether or not all of the region has been employed, the next adjacent region to the right hand side is exposed. This pattern is repeated until the region at the right hand end has been employed the $n+1^{th}$ time, and the $n^{th}$ region is then next employed for imaging. Imaging is next performed in the region that was employed the $n-1^{th}$ time. As the radiation detection section 106 continues to be employed in this manner, the region employed the previous time is not employed for imaging the next time, and distribution of the usage status can be achieved. Since the exposure surface area is the same each time imaging is performed, control by the cassette controller 128 to rotate the motor and the take-up sections is similar control each time, thereby raising processing speed.

Figure 11:
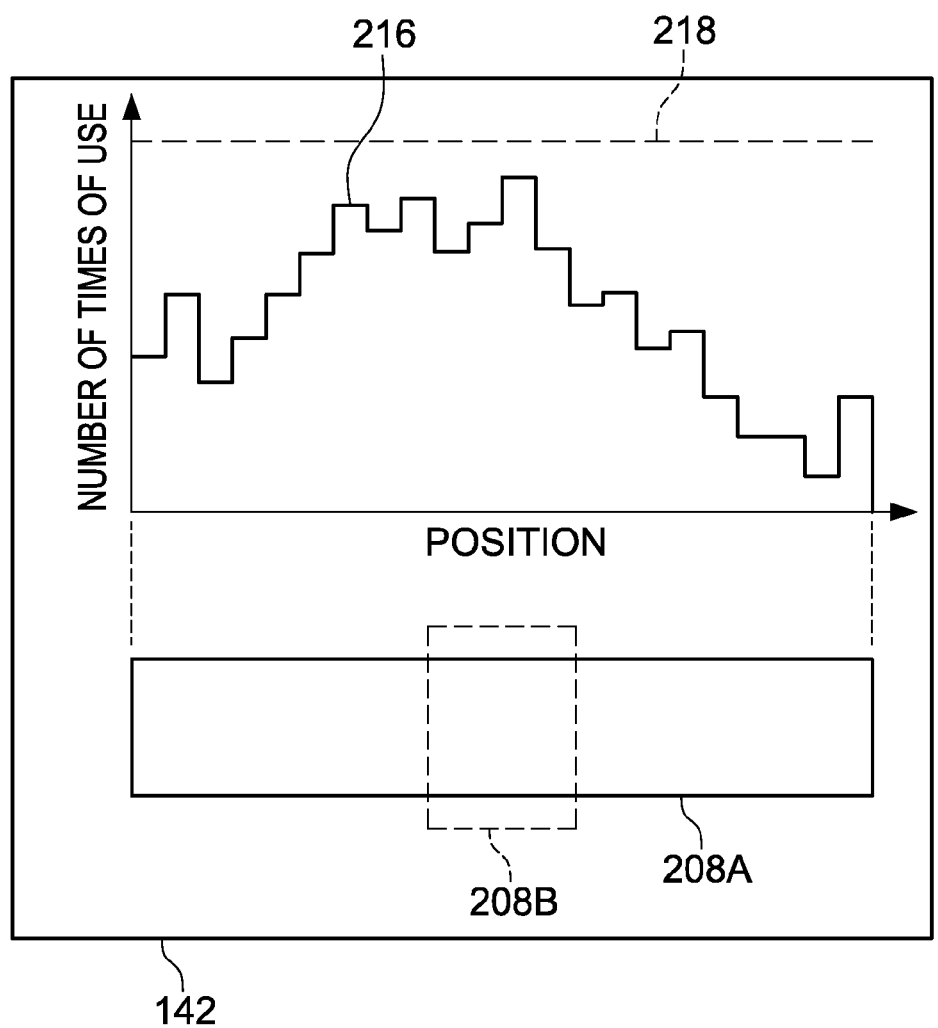
FIG. 11 is an example of a display wherein the usage status of a radiation detection section is displayed using a display section.

Explanation follows regarding another example of exposure position change operation of the radiation detection section 106 when imaging is performed plural times using the electronic cassette 100, with reference to FIG. 11. FIG. 11 is an example of a display on the display section 142. The section above the region showing the total region 208A, the exposure surface area and exposure position 208B of the radiation detection section 106, shows a graph 216 displayed on the display section 142 with the region of the radiation detection section 106 on the horizontal axis and the number of times of use for each region of the radiation detection section 106 shown on the vertical axis. The graph 216 is a graphical representation of the results of number of times of use of the radiation detection section 106, stored in units of 1 cm. The intermittent line 218 indicates an upper limit to the recommended number of times of use for the radiation detection section 106. A user is thereby able to refer to the graph 216 and select an exposure position where there is a small number of times of use. In particular, when the user employing the electronic cassette 100 this time is different from the user the previous time, the usage status of the radiation detection section 106 can be readily ascertained at a glance by viewing the graph 216 since how many times given regions were employed by the previous user is also stored. Moreover, displaying the usage status on the display section 142 in different colors depending on the user enables the regions predominantly used by each user to be ascertained.

Configuration may be made such that the imaging site or the surface area to be employed in imaging is specified by a user, and the electronic cassette 100 automatically determines and controls to externally expose the radiation detection section 106 at the most appropriate exposure position for the imaging site or surface area to be employed in imaging. More specifically the cassette controller 128 determines as the exposure position the region with the lowest total number of times of use for the exposure surface area employed, based on an exposure surface area determined according to the specified imaging site or surface area, and the stored times of use for each 1 cm of the entire region of the radiation detection section 106. For example, when imaging is performed at a feed-out width of 10 cm in the feed-out direction, the cassette controller 128 stores the sum of the number of times of use for a 10 cm portion from the left end of the total region of the radiation detection section 106. The cassette controller 128 then stores the sum of the number of times of use displaced to the right by 1 cm from the computed region. The cassette controller 128 continues this operation in sequence storing the sum of the respective number of times of use for each region up to the right hand end. The cassette controller 128 then determines the exposure position as the region with the lowest sum of number of times of use. The cassette controller 128 controls the rotation of the take-up section 108 and the take-up section 110 such that the determined exposure position is exposed. The cassette controller 128 thereby automatically determines the exposure position with the least number of times of use, and the number of times of use can be evened out for each of the regions of the radiation detection section 106 without particularly involving the user. Usage is accordingly enabled that evens out the amount of deterioration due to radiographic imaging of each region of the radiation detection section 106. The cassette controller 128 may be controlled to determine that use is not possible for regions exceeding the upper limit of recommended times of use, and control such that this region is not externally exposed. Such control eliminates a user employing a region where there is a possibility of image quality deterioration occurring.

Note that while methods for changing the exposure position of the radiation detection section when plural imaging is performed has been given with reference to FIG. 8 to FIG. 11, there is no need for a single of these methods to be employed continuously, and a user may freely select the change method. In particular, after starting use, the control explained with respect to FIG. 11 is preferably employed after repeatedly performing imaging several times using the control explained with respect to FIG. 8 to FIG. 10. Depending on the user's manner of use, it is possible for unevenness in degree of deterioration of the radiation detection section 106 to occur even when control as explained with respect to FIG. 8 to FIG. 10 is performed. In such cases, as explained with respect to FIG. 11, evening out of the usage status can be achieved even for a radiation detection section 106 where unevenness in usage status has already occurred by the cassette controller 128 ascertaining the precise usage status of the radiation detection section 106 and controlling to employ the regions with the least number of times of use. A substantially similar image quality can thereby be achieved even with a radiation detection section 106 where differences in image quality have occurred between each region.

Note that in the present exemplary embodiment, configuration is made with a radiation detection section 106 employing solid-state detection elements for converting radiation into electrical signals, referred to as a direct conversion type, however the radiation detection section 106 is not necessarily limited to a direct conversion type as long as radiographic image data is obtained. For example, configuration may be made with an indirect conversion type employing a scintillator that first converts radiation into visible light and solid state detection elements that then convert the visible light into electrical signals. A phosphor with a base of a material such as GOS ($Gd_2O_2S$:Tb) or CsI:Tl may be employed for the scintillator. A plastic scintillator may also be employed as the scintillator. For example, radiation can be measured without requiring a wavelength conversion agent if a polyethelene terephthalate is employed. In the case of indirect conversion types, the radiation detection section 106 is formed by stacking a scintillator and a photoelectric conversion layer formed with a TFT array and employing solid state detection elements made from a substance such as amorphous silicon for converting visible light into electrical signals. Note that flexible CMOSs (for example an organic CMOS) may be employed as solid state detection elements.

Explanation follows regarding a configuration of the radiation detection section 106 in a case where an indirect conversion type is employed. Note that in the following explanation, portions corresponding to the configuration of the electronic cassette 100 and the radiation detection section 106 of the first exemplary embodiment (FIG. 1 to FIG. 4) are allocated the same reference numerals.

Figure 17:
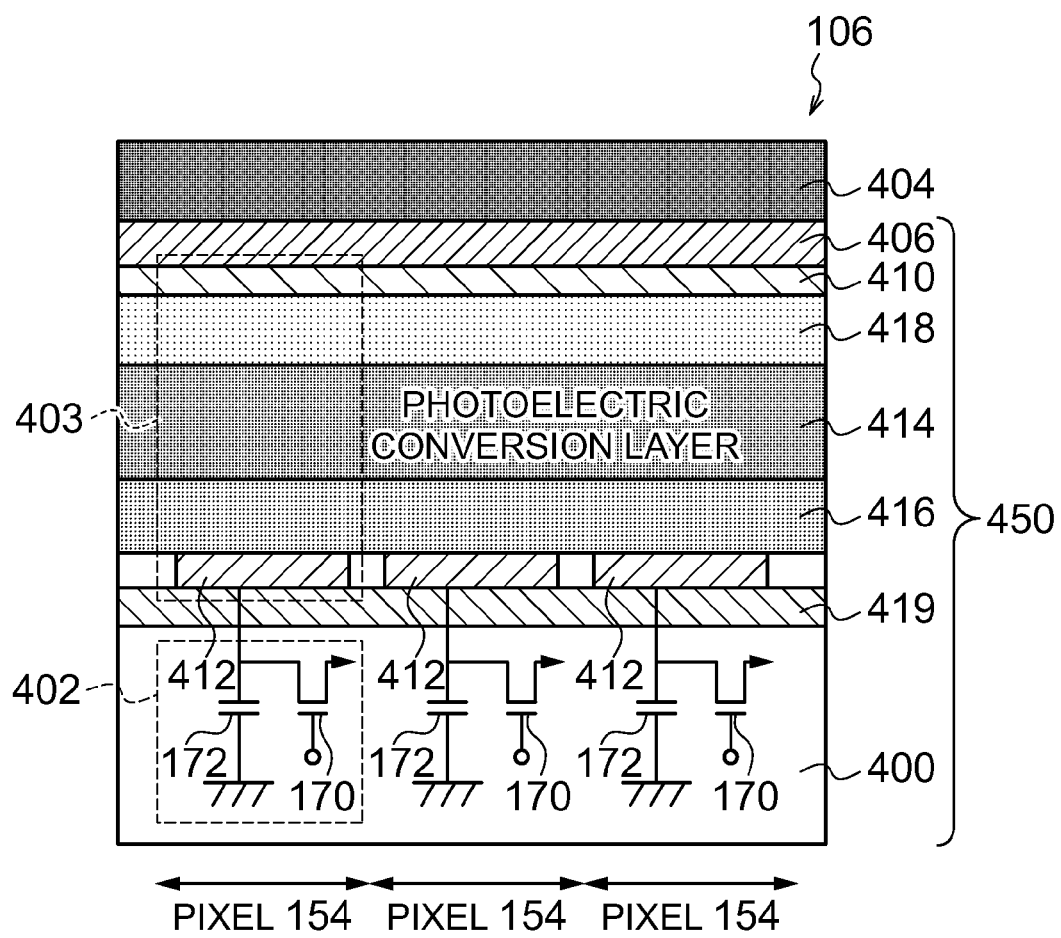
FIG. 17 is a schematic cross-section illustrating a schematic configuration of an indirect conversion method radiation detection section.

FIG. 17 is a schematic cross-section illustrating an outline configuration of a portion consisting of 3 pixels 154 of the indirect conversion type radiation detection section 106.

The radiation detection section 106 includes signal output sections 402, sensor sections 403 and a scintillator 404 stacked in sequence on a flexible insulating substrate 400. Pixels 154 are configured by the signal output sections 402 and the sensor sections 403. Plural of the pixels 154 are arrayed on the substrate 400 in a configuration in which the signal output sections 402 and the sensor sections 403 of each of the pixels 154 overlap with each other.

The scintillator 404 is formed on the sensor sections 403 with a transparent insulator film 406 interposed therebetween. The scintillator 404 is formed by film forming a phosphor that converts incident radiation into light and emits the light. Due to provision of such a scintillator 404, radiation that has passed through an imaging subject is absorbed and light emitted.

The wavelength region of the light emitted by the scintillator 404 is preferably in the visible light region (wavelengths of 360 nm to 830 nm). The wavelength region more preferably includes a green wavelength region in order to enable monochrome imaging by the radiation detection section 106.

As the phosphor used for the scintillator 404, specifically when imaging using X-rays as the radiation, a phosphor including cesium iodide (CsI) is preferably employed, and CsI (Tl) with an emission spectrum of 420 nm to 700 nm when irradiated with X-rays is particularly preferably employed. The emission peak wavelength in the visible light region of CsI (Tl) is 565 nm.

The scintillator 404 may be formed by deposition on a deposition substrate in order, for example, to form columnar crystals of CsI (Tl). When the scintillator 404 is thus formed by deposition an Al plate is often employed as the deposition substrate from the perspectives of X-ray transmissivity and cost, however there is no limitation thereto. Note that when GOS is employed as the scintillator 404, the scintillator 404 may be formed by coating the GOS without employing a deposition substrate.

The sensor sections 403 include an upper electrode 410, lower electrodes 412 and a photoelectric conversion layer 414 disposed between the upper and lower electrodes.

The upper electrode 410 is preferably configured by a conducting material that is transparent at least with respect to the emission wavelength of the scintillator 404 because it is necessary to allow the light emitted by the scintillator 404 to be incident to the photoelectric conversion layer 414. More specifically, preferably a transparent conducting oxide (TCO) with high transmittance to visible light and low resistance is employed for the upper electrode 410. A metal thin film such as of Au may also be used as the upper electrode 410, but TCO is preferred since the resistance of a metal thin film is liable to increase when trying to obtain a transmittance of 90% or more. Examples of materials preferably employed include ITO, IZO, AZO, FTO, $SnO_2$, $TiO_2$ and $ZnO_2$. ITO is most preferred from the standpoints of ease of processing, low resistance, and transparency. The upper electrode 410 may be configured as a single layer common to all the pixels 154 or may be divided per pixel 154.

The photoelectric conversion layer 414 absorbs light emitted from the scintillator 404, and generates charge according to the absorbed light. The photoelectric conversion layer 414 may be formed from any material that generates electric charge on illumination with light, and may, for example, be formed from amorphous silicon or an organic photoelectric conversion material. When the photoelectric conversion layer 414 includes amorphous silicon, a wide absorption spectrum capable of absorbing light emitted by the scintillator 404 results. When the photoelectric conversion layer 414 includes an organic photoelectric conversion material, a sharp absorption spectrum to the visible region, with virtually no electromagnetic waves other than the light emitted by the scintillator 404 absorbed by the photoelectric conversion layer 414 results. Noise generated as a result of radiation such as X-rays being absorbed by the photoelectric conversion layer 414 can be accordingly be effectively suppressed.

The absorption peak wavelength of the organic photoelectric conversion material configuring the photoelectric conversion layer 414 is preferably as close as possible to the emission peak wavelength of the scintillator 404 so that the organic photoelectric conversion material most efficiently absorbs the light emitted by the scintillator 404. Ideally the absorption peak wavelength of the organic photoelectric conversion material and the emission peak wavelength of the scintillator 404 coincide with each other, however the organic photoelectric conversion material can sufficiently absorb the light emitted from the scintillator 404 as long as any difference therebetween is small. More specifically, the difference between the absorption peak wavelength of the organic photoelectric conversion material and the emission peak wavelength of the scintillator 404 to radiation is preferably within 10 nm, and more preferably within 5 nm.

Examples of organic photoelectric conversion materials capable of satisfying this condition include quinacridone organic compounds and phthalocyanine organic compounds. For example, the absorption peak wavelength in the visible region of quinacridone is 560 nm. It is accordingly possible to make the difference between respective peak wavelengths within 5 nm if quinacridone is used as the organic photoelectric conversion material and CsI (Tl) is used as the material of the scintillator 404. The charge amount generated in the photoelectric conversion layer 414 can thereby be substantially maximized.

Specific explanation follows regarding the photoelectric conversion layer 414 applicable to the indirect conversion type radiation detection section 106.

Electromagnetic wave absorption/photoelectric conversion locations in the indirect conversion type radiation detection section 106 can be configured by the pairs of the lower electrodes 412 and the upper electrode 410 and an organic layer that includes the organic photoelectric conversion layer 414 interposed between the lower electrodes 412 and the upper electrode 410. More specifically, the organic layer can be formed by stacking or mixing such sites as a site where electromagnetic waves are absorbed, a photoelectric conversion site, an electron-transporting site, a hole-transporting site, an electron-blocking site, a hole-blocking site, a crystallization inhibiting site, electrodes and an interlayer contact improver site.

The organic layer preferably contains an organic p-type compound or an organic n-type compound.

Organic p-type semiconductors (compounds) are donor organic semiconductors (compounds) mainly represented by hole-transporting organic compounds, and refer to organic compounds having the property of readily donating electrons. More specifically, organic p-type semiconductors (compounds) refer to the organic compound with the smaller ionization potential when two organic materials are brought into contact with each other in use. Consequently, any organic compound can be used as the donor organic compound provided it is an electron-donating organic compound.

Organic n-type semiconductors (compounds) are accepter organic semiconductors (compounds) mainly represented by electron-transporting organic compounds, and refer to organic compounds having the property of readily accepting electrons. More specifically, organic n-type semiconductors (compounds) refer to the organic compound with the greater electron affinity when two organic compounds are brought into contact with each other in use. Consequently, any organic compound can be used as the accepter organic compound provided it is an electron-accepting organic compound.

Detailed description of materials applicable as the organic p-type semiconductor and the organic n-type semiconductor, and for configuring the photoelectric conversion layer 414, is given in JP-A No. 2009-32854, so further description is omitted. The photoelectric conversion layer 414 may also be formed so as to further contain fullerenes or carbon nanotubes.

The thickness of the photoelectric conversion layer 414 is preferably as large a film thickness as possible from the standpoint of absorbing light from the scintillator 404. However, when the thickness of the photoelectric conversion layer 414 reaches a certain thickness or greater, the strength of the electric field generated in the photoelectric conversion layer 414 by bias voltage applied from both ends of the photoelectric conversion layer 414 drops, and electric charge can no longer be collected. The thickness of the photoelectric conversion layer 414 is accordingly preferably from 30 nm to 300 nm. The thickness of the photoelectric conversion layer 414 is more preferably from 50 nm to 250 nm, and is particularly preferably from 80 nm to 200 nm.

In the radiation detection section 106 shown in FIG. 17, the photoelectric conversion layer 414 is a single layer configuration common to all the pixels 154, but the photoelectric conversion layer 414 may also be divided for each of the pixels 154.

The lower electrodes 412 are thin films divided for each of the pixels 154. The lower electrodes 412 can be configured by a transparent or opaque conducting material, and materials such as aluminum or silver can be suitably employed as the lower electrodes 412.

The thickness of the lower electrodes 412 can, for example, be 30 nm to 300 nm.

In the sensor sections 403, one type of electric charge (holes or electrons) out of the electric charges generated in the photoelectric conversion layer 414 can be moved to the upper electrode 410 and the other type can be moved to the lower electrodes 412 by applying a specific bias voltage across the upper electrode 410 and the lower electrodes 412. In the radiation detection section 106 of the present exemplary embodiment, a wiring line is connected to the upper electrode 410, and the bias voltage is applied to the upper electrode 410 through the wiring line. The polarity of the bias voltage is determined such that the electrons generated in the photoelectric conversion layer 414 move to the upper electrode 410 and the holes move to the lower electrodes 412, however the polarities may be reversed.

It is sufficient for each of the sensor sections 403 configuring each of the pixels 154 to include at least the lower electrode 412, the photoelectric conversion layer 414, and the upper electrode 410. However, in order to suppress an increase in dark current, preferably at least an electron-blocking film 416 and/or a hole-blocking film 418 are provided in each of the sensor sections 403, and more preferably both are provided.

The electron-blocking film 416 can be disposed between the lower electrodes 412 and the photoelectric conversion layer 414. Electrons are accordingly suppressed from being injected from the lower electrodes 412 into the photoelectric conversion layer 414 when the bias voltage is applied between the lower electrodes 412 and the upper electrode 410, so dark current can be suppressed from increasing.

Electron-donating organic materials can be used for the electron-blocking film 416.

In practice, it is sufficient for the material that used for the electron-blocking film 416 to be selected in accordance with, for example, the material of the adjacent electrode and the material of the adjacent photoelectric conversion layer 414. A material whose electron affinity (Ea) is greater by 1.3 eV or more than the work function (Wf) of the material of the adjacent electrode and has an ionization potential (Ip) equal to or smaller than the ionization potential of the material of the adjacent photoelectric conversion layer 414 is preferable. Detailed description is given of materials applicable as the electron-donating organic material in JP-A No. 2009-32854, so further explanation is omitted.

The thickness of the electron-blocking film 416 is preferably from 10 nm to 200 nm in order to reliably exhibit a dark current suppressing effect and to prevent a drop in the photoelectric conversion efficiency of the sensor sections 403. The thickness of the electron-blocking film 416 is more preferably from 30 nm to 150 nm, and particularly preferably from 50 nm to 100 nm.

The hole-blocking film 418 can be disposed between the photoelectric conversion layer 414 and the upper electrode 410. Holes can thereby be suppressed from being injected from the upper electrode 410 into the photoelectric conversion layer 414 when the bias voltage is applied between the lower electrodes 412 and the upper electrode 410, enabling dark current to be suppressed from increasing.

Electron-accepting organic materials can be used for the hole-blocking film 418.

The thickness of the hole-blocking film 418 is preferably from 10 nm to 200 nm in order to allow the hole-blocking film 418 to reliably exhibit a dark current suppressing effect and to prevent a drop in the photoelectric conversion efficiency of the sensor sections 403. The thickness of the hole-blocking film 418 is more preferably from 30 nm to 150 nm, and particularly preferably from 50 nm to 100 nm.

In practice, it is sufficient for the material employed for the hole-blocking film 418 to be selected in accordance with, for example, the material of the adjacent electrode and the material of the adjacent photoelectric conversion layer 414. A material whose ionization potential (Ip) is greater by 1.3 eV or more than the work function (Wf) of the material of the adjacent electrode and has an electron affinity (Ea) equal to or greater than the electron affinity of the material of the adjacent photoelectric conversion layer 414 is preferable for the material employed for the hole-blocking film 418. Detailed description of materials applicable as the electron-accepting organic material are given in JP-A No. 2009-32854, so further description is omitted.

The positions of the electron-blocking film 416 and the hole-blocking film 418 may be reversed when the bias voltage is set such that, out of the electric charges generated in the photoelectric conversion layer 414, it is the holes that move to the upper electrode 410 and the electrons that move to the lower electrode 412. The electron-blocking film 416 and the hole-blocking film 418 need not both be provided, and a certain degree of a dark current suppressing effect can be obtained as long as one or other is provided.

The signal output sections 402 are formed on the surface of the substrate 400 below the lower electrode 412 of each of the pixels 154.

Figure 18:
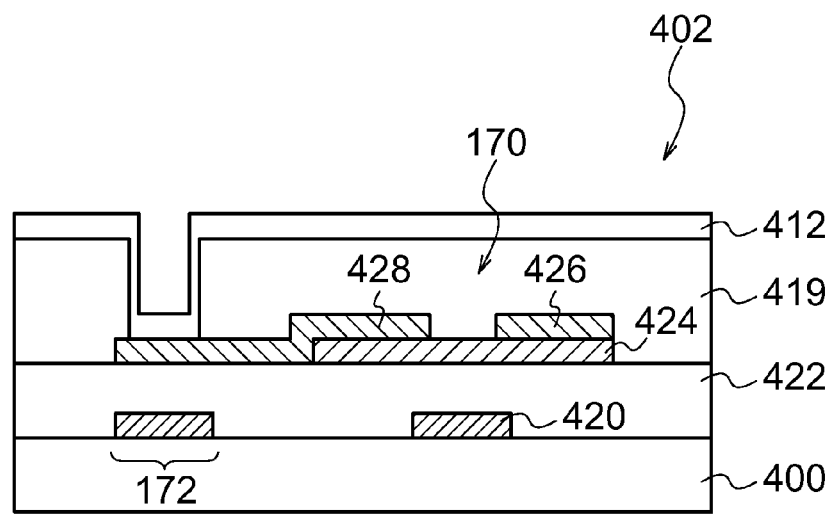
FIG. 18 is a cross-section illustrating a schematic configuration of a signal output section.

FIG. 18 schematically shows a configuration of one of the signal output sections 402.

Each of the signal output sections 402 is configured with a storage capacitor 172 and a TFT 170 corresponding to the lower electrode 412. The storage capacitor 172 stores the electric charge that has moved to the lower electrode 412. The TFT 170 converts the electric charge stored in the storage capacitor 172 into an electric signal and outputs the electric signal. The region where the storage capacitor 172 and the TFT 170 are formed has a portion that overlaps the lower electrode 412 in a plan view. Due to such a configuration, the signal output section 402 and the sensor section 403 in each of the pixels 154 overlap with each other in the thickness direction. The region where the storage capacitor 172 and the TFT 170 are formed is preferably completely covered by the lower electrode 412 in order to keep the planar surface area of the pixels 154 of the radiation detection section 106 small.

The storage capacitor 172 is electrically connected to the corresponding lower electrode 412 via a wiring line of a conductive material that is formed penetrating an insulating film 419 disposed between the substrate 400 and the lower electrode 412. The electric charge trapped by the lower electrode 412 can thereby be moved to the storage capacitor 172.

The TFT 170 is stacked with a gate electrode 420, a gate insulating film 422, and an active layer (channel layer) 424. A source electrode 426 and a drain electrode 428 are formed a specific spacing apart from each other on the active layer 424. The active layer 424 can, for example, be formed from a material such as amorphous silicon, an amorphous oxide material, an organic semiconductor material or carbon nanotubes. The material configuring the active layer 424 is however not limited thereto.

Possible amorphous oxide materials for configuring the active layer 424 are preferably oxide materials including at least one of In, Ga, and Zn (for example In—O amorphous oxide materials), and oxide materials including at least two of In, Ga, and Zn (for example In—Zn—O amorphous oxide materials, In—Ga—O amorphous oxide materials, or Ga—Zn—O amorphous oxide materials) are more preferred, with oxide materials including In, Ga, and Zn particularly preferred. As such an In—Ga—Zn—O amorphous oxide material, an amorphous oxide material whose composition in a crystalline state would be expressed by $InGaO_3(ZnO)_m$ (where m is an integer less than 6) is preferred and $InGaZnO_4$ is particularly preferred. Note that possible amorphous oxide materials for configuring the active layer 424 are not limited thereto.

Examples of possible organic semiconductor materials for configuring the active layer 424 include phthalocyanine compounds, pentacene, vanadyl phthalocyanine, and dioxaanthanthrene compounds such as peri-xanthenoxanthene derivatives, however there is no limitation thereto. Detailed description of configurations of phthalocyanine compounds are given in JP-A No. 2009-212389, so further description thereof is omitted. Detailed description of configurations of dioxaanthanthrene compounds are also given in JP-A No. 2010-6794, so further description thereof is omitted Radiation such as X-rays is not absorbed, or is restricted to extremely minute absorption, when the active layer 424 of the TFT 170 is formed from an amorphous oxide material, an organic semiconductor material, or carbon nanotubes. The generation of noise in the signal output section 402 can accordingly be effectively suppressed.

The switching speed of the TFT 170 can also be increased and the TFT 170 can be formed with a low degree of absorption of light in the visible light region when the active layer 424 is formed with carbon nanotubes. When the active layer 424 is formed with carbon nanotubes, the performance of the TFT 170 drops significantly even when an extremely minute amount of metal impurity is mixed into the active layer 424. It is therefore necessary to separate, extract, and form extremely high-purity carbon nanotubes such as by using centrifugal separation.

The above amorphous oxide materials, organic semiconductor materials, carbon nanotubes and the organic photoelectric conversion material are all capable of being formed into films at a low temperature. A flexible substrate such as plastic, aramids, or bionanofibers can therefore be employed as the substrate 400. Specifically, flexible substrates such as polyesters, for example polyethylene terephthalate, polybutylene phthalate, and polyethylene naphthalate, polystyrene, polycarbonate, polyethersulphone, polyarylate, polyimide, polycyclic olefin, norbornene resin, and poly(chloro-trifluoro-ethylene) can be employed. Employing such a flexible substrate made of plastic enables a reduction in weight to be achieved, which is advantageous from the perspective of for example portability.

Other layers may also be provided to the substrate 400, such as an insulating layer to secure insulation, a gas barrier layer to prevent the transmission of moisture and/or oxygen, and/or an undercoat layer to improve flatness or adhesion to for example the electrodes.

High-temperature processing at 200 degrees or higher can be applied to aramids, enabling a transparent electrode material to be hardened at a high temperature to give a low resistance, and aramids are also compatible with automatic packaging of driver ICs including solder reflow processing. Aramids also have a thermal expansion coefficient that is close to that of indium tin oxide (ITO) or a glass substrate, so they have little warping after manufacture and do not break easily. Aramids can also form a thinner substrate compared for example to a glass substrate. An ultrathin glass substrate and an aramid may also be layered to form the substrate 400.

Bionanofibers are composites of cellulose microfibril bundles (bacterial cellulose) produced by a bacterium (Acetobacter xylinum) and a transparent resin. Cellulose microfibril bundles have a width of 50 nm, a size that is ⅒ visible wavelengths, and also have high strength, high elasticity, and low thermal expansion. By impregnating and hardening bacterial cellulose in a transparent resin such as an acrylic resin or an epoxy resin, bionanofibers can be obtained that exhibit a light transmittance of about 90% to 500 nm wavelength even when fibers are included at 60 to 70%. Bionanofibers have a low thermal expansion coefficient (3 to 7 ppm) comparable to silicon crystals, a strength comparable to steel (460 MPa), high elasticity (30 GPa), and are flexible, enabling the substrate 400 to be formed thinner than for example a glass substrate.

As shown in FIG. 17 the radiation detection section 106 is formed by forming the signal output sections 402, the sensor sections 403 and the transparent insulator film 406 in sequence on the substrate 400, and by sticking the scintillator 404 onto the substrate 400 by employing for example a low light absorbency adhesive resin. The substrate 400 formed up to the transparent insulator film 406 is referred to below as a TFT active matrix substrate (also sometimes referred to below as TFT substrate) 450.

The indirect conversion type radiation detection section 106 is, as shown in FIG. 3 and FIG. 4, provided with plural pixels 154 that are configured including the above sensor sections 403 and the storage capacitors 172 and are arrayed in two dimensions, in a specific direction (the row direction in FIG. 3) and a direction intersecting with the specific direction (the column direction in FIG. 3).

In the indirect conversion type radiation detection section 106 plural gate lines 158 for switching each of the TFTs 170 ON/OFF are provided extending in the specific direction (row direction) and plural signal lines 162 for reading charge through the TFTs 170 in the ON state are provided extending in the intersecting direction (the column direction).

Each of the gate lines 158 is connected to the electrical circuit 126A through the first flexible wiring section 160 at one width direction end side of the radiation detection section 106, and each of the signal lines 162 is connected to the electrical circuit 126A through the second flexible wiring section 164 at one length direction end side of the radiation detection section 106.

Figure 19:
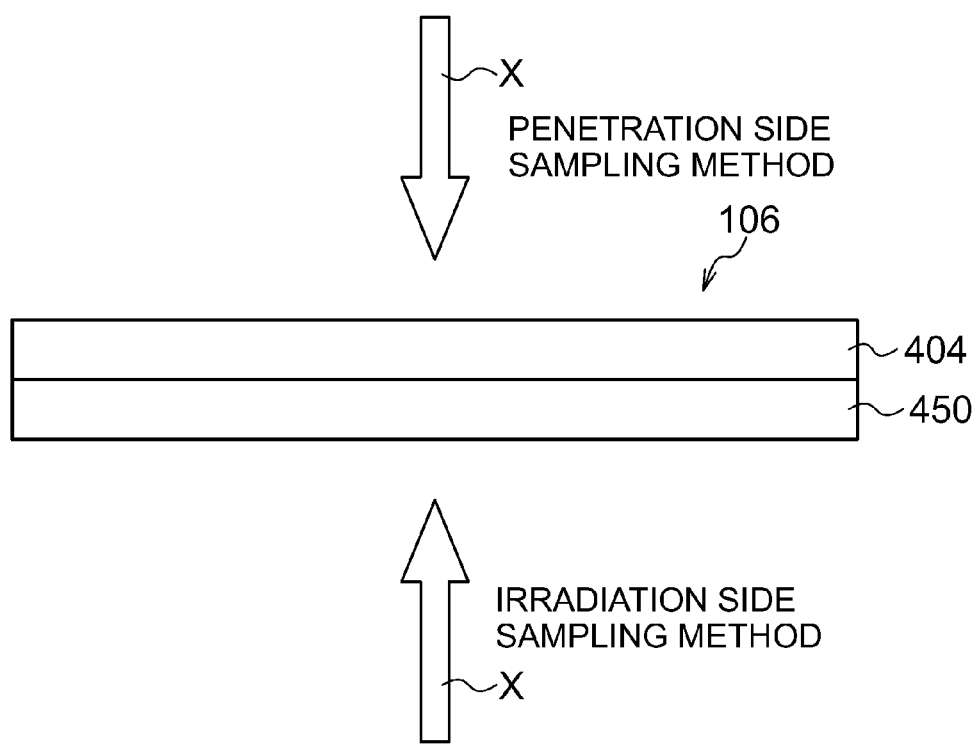
FIG. 19 is a cross-section from viewed from the side to explain an irradiation side sampling method and a penetration side sampling method.

When radiation is irradiated onto the indirect conversion type radiation detection section 106 from the side on which the scintillator 404 is formed, as shown in FIG. 19, and a radiographic image is read by the TFT substrate 450 provided on the back face side with respect to the radiation incident face, namely when using a Penetration Side Sampling (PSS) method, light is emitted with higher intensity at the face of the scintillator 404 on the top side in FIG. 19 (the opposite side to the TFT substrate 450 side). However, when radiation is irradiated from the TFT substrate 450 side in the indirect conversion type radiation detection section 106 and a radiographic image is read by the TFT substrate 450 provided on the front face side with respect to the radiation incident face, namely when using an Irradiation Side Sampling (ISS) method, radiation that has passed through the TFT substrate 450 is incident to the scintillator 404 and light is emitted with higher intensity from the TFT substrate 450 side of the scintillator 404. Each of the sensor sections 403 provided to the TFT substrate 450 generates charges due to the light generated in the scintillator 404. The radiation detection section 106 therefore gives a higher resolution of captured radiographic images when a PSS method is employed than when an ISS method is employed, since the light emission position of the scintillator 404 is closer to the TFT substrate 450.

The radiation detection section 106 is configured with the photoelectric conversion layer 414 of the sensor sections 403 formed from an organic photoelectric conversion material and so radiation is barely absorbed by the photoelectric conversion layer 414. The amount of radiation absorbed by the photoelectric conversion layer 414 is low even when radiation passes through the TFT substrate 450 due to employing an ISS method. Any drop in sensitivity to X-rays can hence be suppressed. When the photoelectric conversion layer 414 of the TFT substrate 450 is thus configured from an organic photoelectric conversion material, an ISS method may be applied since hardly any radiation is absorbed in the photoelectric conversion layer 414 and radiation attenuation can be suppressed to a small amount.

Both the amorphous oxide material configuring the active layer 424 of the TFTs 170 and the organic photoelectric conversion material configuring the photoelectric conversion layer 414 can be formed using film forming at low temperature. The substrate 400 can accordingly be made from plastic resin, aramid and/or bionanofibers, having low absorptivity to radiation. Since the amount of radiation absorbed by the thus formed substrate 400 is small, sensitivity to X-rays can be suppressed from deteriorating even when radiation passes through the TFT substrate 450 due to employing an ISS method.

The photoelectric conversion layer 414 of the indirect conversion type radiation detection section 106 is accordingly configured, for example, with an organic photoelectric conversion material, and the active layer 424 of each of the TFTs 170 is configured with an amorphous oxide material. The substrate 400 is also formed from a flexible substrate with low radiation absorption, such as a flexible substrate formed from a plastic resin, aramid, or bionanofibers.

Figure 20:
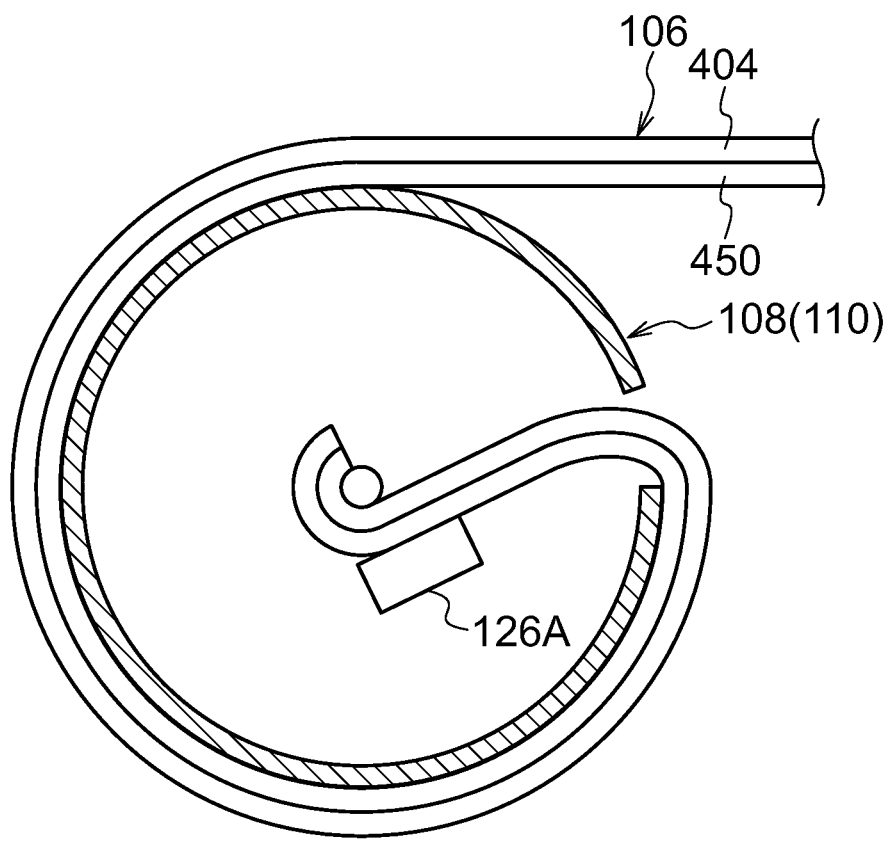
FIG. 20 is a cross-section illustrating a radiation detection section that has been taken up into a take-up section in a state such that a TFT substrate is on the inside.

In the electronic cassette 100, as shown in FIG. 20, the radiation detection section 106 is wound on the take-up section 108 and the take-up section 110 such that the TFT substrate 450 is on the inside of the radiation detection section 106. Thereby, as shown in FIG. 7, during imaging, the radiation detection section 106 is fed out with the casing 102 and the casing 104 separated from each other, the patient 210 is placed on the fed-out radiation detection section 106, and radiation is irradiated from the radiation irradiation section 212 above the patient 210. In such cases the TFT substrate 450 is on the patient 210 side of the radiation detection section 106, such that imaging is performed by an ISS method.

Figure 21:
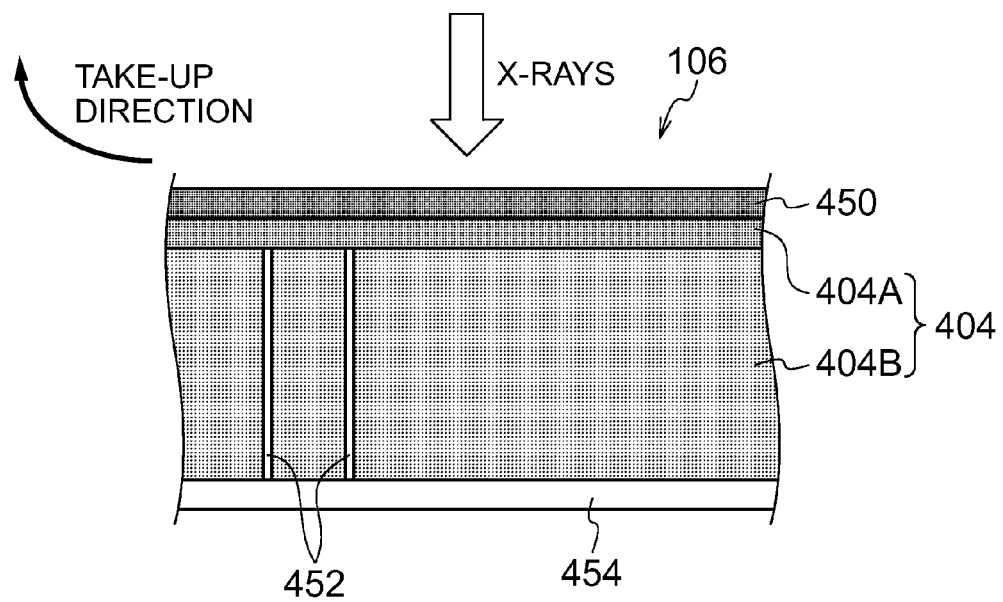
FIG. 21 is a cross-section illustrating an example of a configuration in a case wherein a scintillator of a radiation detection section is formed from columnar crystals.
Figure 22:
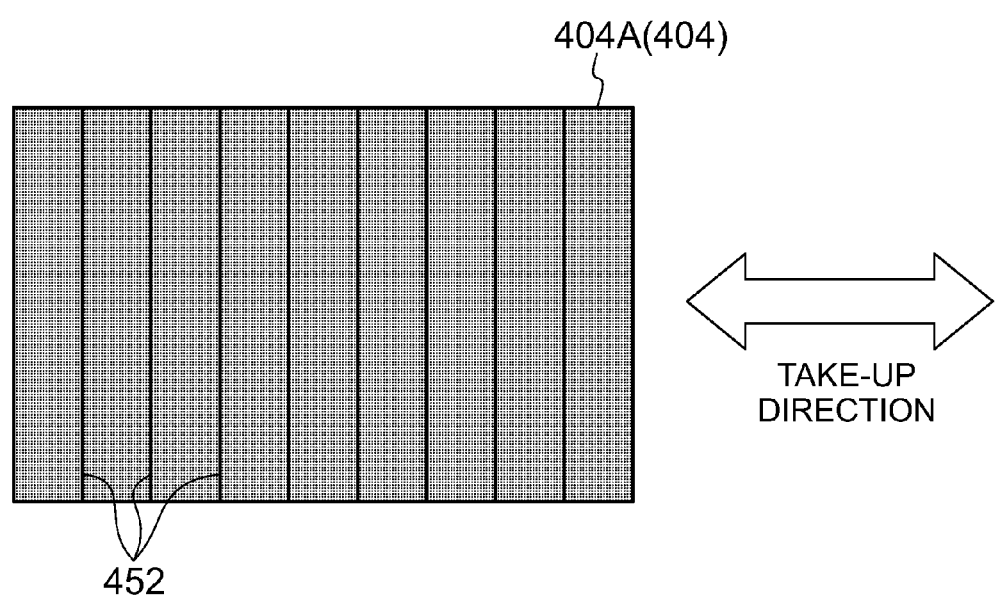
FIG. 22 is a plan view illustrating an example of a configuration in a case wherein a scintillator of a radiation detection section is formed from columnar crystals.

The scintillator 404 may be formed by columnar crystals of CsI:Tl. The scintillator 404 cannot be taken up on the take-up section 108 and the take-up section 110 as it is, due to columnar crystals of CsI:Tl being hard and brittle. Therefore for example, as shown in FIG. 21, to configure the scintillator 404 on the TFT substrate 450, a non-columnar crystal region 404A is formed and a columnar crystal region 404B is then formed thereon. Then, for example as shown in FIG. 21 and FIG. 22, parallel partings 452 are cut in the columnar crystal region 404B of the scintillator 404, employing for example laser cutting, in a direction orthogonal to the take-up direction of the take-up section 108 and the take-up section 110, at a specific depth and at specific intervals such that the columnar crystals of the columnar crystal region 404B do not break when the scintillator 404 is taken up on the take-up section 108 and the take-up section 110. The surface of the columnar crystal region 404B side of the scintillator 404 is also sealed by a resilient protection sheet 454. As shown in FIG. 20, such a radiation detection section 106 formed with the scintillator 404 is taken up on the take-up section 108 and the take-up section 110 such that the TFT substrate 450 is on the inside of the radiation detection section 106. Due to providing the non-columnar crystal region 404A in the scintillator 404, the columnar crystals of CsI:Tl in the columnar crystal region 404B are prevented from being broken up from each other, and the partings 452 portions can be suppressed from leading to gaps in images during imaging. The radiation detection section 106 can be taken up on the take-up section 108 and the take-up section 110 due to providing the partings 452 in the columnar crystal region 404B of the scintillator 404. By taking up the scintillator 404 on the take-up section 108 and the take-up section 110 such that the TFT substrate 450 is on the inside of the scintillator 404, the respective columnar crystals in the columnar crystal region 404B can be prevented from rubbing against each other.

Figure 23:
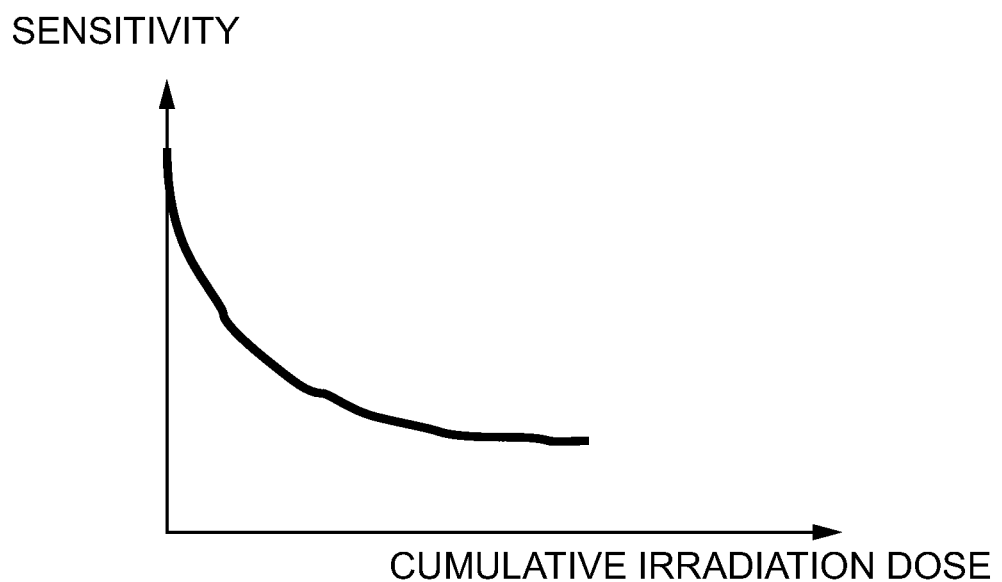
FIG. 23 is a graph illustrating a relationship between the cumulative irradiated dose and sensitivity of CsI.

As shown in FIG. 23, the sensitivity of CsI falls as the cumulative irradiated dose increases when performing successive imaging. This drop in sensitivity recovers when left to stand in a non-radiation-irradiated state, and recovery is accelerated by holding in a high temperature environment.

However, even when there is a drop in the sensitivity of the scintillator 404 of the radiation detection section 106 taken up on the take-up section 108, as shown in FIG. 20, recovery can be accelerated using the heat from the electrical circuit 126A accommodated inside the hollow section 120 by taking up the radiation detection section 106 in the take-up section 108.

Note that while explanation has been given of a case in the first exemplary embodiment in which, as shown in FIG. 3, the electrical circuit 126A installed with the line scan drive section 174 and the readout circuit 130 is provided at a length direction end portion of the radiation detection section 106, and each of the gate lines 158 of the radiation detection section 106 is connected to the electrical circuit 126A through the first flexible wiring section 160, and each of the signal lines 162 of the radiation detection section 106 is connected to the electrical circuit 126A through the second flexible wiring section 164, there is no limitation thereto.

The drive circuits, such as the line scan drive section 174 and the readout circuit 130 have hitherto been configured from hard silicon driver ICs. However switching elements such as the TFTs 170 can be flexibly formed to a substrate by configuring the active layer 424 of the TFT 170 as described above, for example formed from an amorphous silicon or amorphous oxide material, organic semiconductor material or carbon nanotubes.

As shown in FIG. 24, the line scan drive section 174 employing switching elements such as TFTs may, for example, be formed at one width direction side of the radiation detection section 106, so as to drive each of the gate lines 158. The flexibility of the radiation detection section 106 can thereby be maintained even when drive circuits such as the line scan drive section 174 and the readout circuit 130 are formed to the radiation detection section 106.

Note that while in the present exemplary embodiment the radiation detection section 106 is accommodated in the casing 102 or the casing 104 by winding the radiation detection section 106 on the take-up section 108 or the take-up section 110, any configuration may be employed as long as the radiation detection section 106 can be accommodated in the casing 102 and the casing 104 and the radiation detection section 106 can be fed out from the casing 102 or the casing 104. For example, a mechanism may be employed for accommodating the radiation detection section 106 folded inside the casing 102 or the casing 104. In such cases, a drive mechanism for accommodating the radiation detection section 106 and a drive mechanism for folding the radiation detection section 106 may be provided inside the casing 102 and/or the casing 104. A conceivable drive mechanism for folding is, for example, a mechanism that nips the radiation detection section 106 from above and below, and achieves a folded state by moving the radiation detection section 106 in a direction orthogonal to the feed-out direction. A concertina structure may also be applied as a housing mechanism.

Note that while a motor is provided to both the casing 102 and the casing 104 in the present exemplary embodiment, the motor(s) may be dispensed with. When no motor is provided, a user manually switches the stoppers to OFF, and manually feeds out the radiation detection section 106 from the casing 102 or the casing 104 while ascertaining the exposure surface area by watching the display section 142. In such cases the casing 102 and the casing 104 are preferably configured such that when the exposure surface area reaches the surface area specified by the input section 136 an alarm rings, or the stoppers are switched ON automatically. When no motor is provided in the casing 102 and/or the casing 104, preferably configuration is made such that the automatic take-up and feed-out mechanisms of the radiation detection section 106 described in the first exemplary embodiment can be added. When such an approach is adopted a cost saving of the amount of the automatic take-up and feed-out mechanism can be achieved, and yet if a user then desires provision of the automatic take-up and feed-out mechanism after purchase of the electronic cassette, this can be accommodated by additionally installing a new automatic take-up and feed-out mechanism. Preferably a take-up drive lever capable of manually taking up the radiation detection section 106 is provided in cases without motors. When no motor is provided a saving of the motor cost can be achieved and power consumption can be lowered.

A single motor may be provided alone to either the casing 102 or the casing 104. Automatic operation can be performed in the electronic cassette provided with only one motor, other than control to accommodate the radiation detection section 106 in the casing not provided with a motor. For example, when a given region has been employed for imaging and it is desired to change the exposure position for the next imaging, the electronic cassette can change the exposure position of the radiation detection section 106 by taking up the same surface area of the radiation detection section 106 as the region employed the previous time in the casing provided with a motor. In the electronic cassette, the exposure surface area can also be made larger than the surface area of the region employed the previous time by taking up more surface area than the surface area employed the previous time and then feeding out a smaller amount. When it is desired to employ a smaller exposure surface area than the surface area of the region employed the previous time, the electronic cassette can achieve this by taking up more of the radiation detection section 106 than the surface area employed the previous time. Thus when imaging in the direction in which the radiation detection section is taken up into the casing provided with the motor, the electronic cassette can automatically change the exposure surface area and the exposure position. When taking up the radiation detection section 106 in the direction towards the casing not provided with the motor, a user can manually move the take-up drive lever to perform take-up or feed-out of the radiation detection section 106, and thereby adjust the exposure surface area. Preferably a user is notified, such as by an alarm sounding, that the pre-set exposure surface area has been reached when the user is performing manual take-up or feed-out. When a motor is only provided inside one of the casings in this manner, the electronic cassette can perform automatic control of the exposure surface area and exposure position when the electronic cassette performs imaging in the take-up direction towards the casing provided with the motor. The electronic cassette 100 can also automatically achieve the accommodated state of the radiation detection section 106. When a motor is only provided inside one of the casings, preferably a mechanism capable of generating electricity by rotation of a take-up drive lever is provided inside the casing not provided with the motor, such that a battery can be recharged by rotating the lever. Such a configuration enables the electronic cassette to adjust the exposure surface area and the exposure position automatically for imaging in the direction automatically adjustable by motor, and enables a user to adjust the exposure surface area and exposure position by rotating the take-up drive lever for imaging in the direction not automatically adjustable by motor, while the electronic cassette also recharges the battery at the same time.

In the present exemplary embodiment the battery 146 is only provided to the casing 102, however a detachable battery may be mounted to both the casing 102 and the casing 104. When a battery is provided to both the casing 102 and the casing 104, even when one or other batteries goes flat, a new battery can be brought in without losing power, known as a hot-swap. Providing a battery to both the casing 102 and the casing 104 reduces the difference in weight between the casing 102 and the casing 104, thereby raising the overall weight balance of the electronic cassette 100.

Note that while stoppers are provided to both the casing 102 and the casing 104 in the present exemplary embodiment configuration may be made with a stopper provided only to one casing. In such cases the single stopper controls whether or not take-up or feed-out of the radiation detection section 106 is possible.

Note that in the present exemplary embodiment the cassette controller 128 stores the exposure surface area and the exposure position of the radiation detection section 106 in the usage status storage section 139 each time imaging is performed. However any method may be applied as long as the usage status of each of the regions of the radiation detection section 106 and the region used the previous time can be ascertained. Storing the exposure surface area and the exposure position does not necessarily have to be performed automatically by the apparatus. For example, a mode may be adopted in which a user takes a memo when looking at the exposure surface area and the exposure position displayed on the display section 142, and then inputs the exposure surface area and the exposure position to the electronic cassette 100 later. There is also no necessity for this to be performed every time of use.

The electronic cassette 100 according to the present exemplary embodiment is capable of ascertaining the exposure surface area and the exposure position of the radiation detection section 106. Configuration may accordingly be made such that data identifying the exposure surface area and/or the exposure position of the radiation detection section 106 are incorporated as metadata in the radiographic image data obtained by imaging and stored in the image storage section 137. Adopting such an approach enables a user to identify whether or not there is a problem with a given region of the radiation detection section 106 when a problem in the radiation detection section 106 is discovered by looking at the captured images. In such cases, preferably a user is able to input to the electronic cassette 100 a region of the radiation detection section 106 in which a problem has occurred as a region suffering deterioration due to radiation (referred to below as a deteriorated region). On receipt of a deteriorated region input by a user, the electronic cassette 100 with an identified deteriorated region preferably then controls the exposure position on the radiation detection section such that the deteriorated region is not used. Adopting such control means that a region where deterioration has been confirmed to have occurred is not employed again, enabling image quality problems to be prevented from occurring. The electronic cassette 100 that has received input of a deteriorated region from a user preferably displays the region where deterioration has occurred on the display section 142. For example, the display section 142 could display a region where deterioration has occurred such as by coloring black in 208A of FIG. 6. Such display enables a user to ascertain deteriorated regions of the radiation detection section 106 at a glance. In such cases preferably the electronic cassette 100 displays a maintenance prompt to a user on the display section 142 as the number of deteriorated regions increases. For example, the electronic cassette 100 could display a recommendation to perform maintenance on the display section 142, emphasized every time the number of deteriorated regions increases.

The electronic cassette 100 may be configured to automatically store identified deteriorated regions, such as on the usage status storage section 139. The deteriorated regions can be computed for example from the generation of a fixed pattern of noise. Another computation method is to determine that a given pixel has deteriorated when the given pixel has a value clearly abnormal in comparison to adjacent pixels. When there is such a clearly abnormal value in the radiographic image data, the electronic cassette 100 does not employ the abnormal value and, for example, employs peripheral pixel values to perform correction. The electronic cassette 100 may also be configured to read the pixel values at a given time interval when no imaging is being performed, such as when in standby, to detect pixels with abnormal values, and to determine that pixels with abnormal values have deteriorated. The electronic cassette 100 preferably renders the deteriorated region unusable also in such cases where deteriorated regions have been identified automatically.

The electronic cassette 100 may incorporate data such as an ID identifying the electronic cassette 100 or the radiation detection section 106 as metadata in the radiographic image data. Such an approach enables identification of whether or not there is a problem with a particular electronic cassette when there are plural electronic cassettes.

The take-up amount detection sensors 140A and 140B according to the present exemplary embodiment compute the rotation angles for the take-up section 108 and the take-up section 110 based on the radial lengths of the take-up section 108 and the take-up section 110, to derive the surface area of the radiation detection section 106 that is taken-up inside the casing 102 or the casing 104, and to identify the position of the casing 102 and the casing 104 with respect to the radiation detection section 106. However, there is no necessity to always store the surface area of the radiation detection section 106 taken up in the casing 102 and the casing 104 and to identify the position of the casing 102 and the casing 104 with respect to the radiation detection section 106. For example, configuration may be made such that a take-up amount detection sensor reads a scale on the radiation detection section 106, and determines the position of the casing 102 or the casing 104 on the radiation detection section 106. A take-up amount detection sensor need not necessarily be provided inside the casing.

In a mode in which the casing 102 or the casing 104 is ascertained to be at a certain position on the radiation detection section 106, an aim for adjustment of the exposure surface area and the exposure position of the radiation detection section 106 can be the position of the casing 102 and the casing 104 with respect to the radiation detection section 106 to achieve. The exposure surface area and the exposure position of the radiation detection section 106 can be adjusted given the position of the casing 102 and the casing 104 on the radiation detection section 106 and with the cassette controller 128 designating the positions to be moved to next. Such a configuration enables the exposure surface area and the exposure position to be adjusted by ascertaining one dimensional positions of the casing 102 and the casing 104 on the radiation detection section 106. In another mode, configuration may be made such the whole region of the radiation detection section 106 is read, and regions whose read data has values that could not be noise or greater are identified as being in the used region. A mode may also be configured with a barcode or the like provided to the radiation detection section 106, and the take-up amount determined by reading the barcode.

Two take-up amount sensors need not always be provided. For example, when the exposure surface area and the exposure position of the radiation detection section 106 is changed on one take-up amount sensor, the position of one casing on the radiation detection section can be ascertained by the take-up amount sensor. The electronic cassette 100 then makes the casing 102 and the casing 104 approach each other, and the electronic cassette 100 can perform feed-out of the radiation detection section 106 from when the exposure surface area of the radiation detection section 106 has become 0. The exposure surface area can accordingly be adjusted by changes in values of a single take-up amount sensor.

The radial length of the take-up section 108 or the take-up section 110 becomes longer as the radiation detection section 106 is wound on. Hence the cassette controller 128 may compute to add to the radius of the take-up section 108 or the take-up section 110 the thickness of the radiation detection section 106 according to the number of layers of the radiation detection section 106 that have been wound on. Adopting such a configuration results in more accurate adjustment of the exposure surface area of the radiation detection section 106.

In the present exemplary embodiment, when imaging is finished the take-up button 196 or the take-up button 198 is used to accommodate the radiation detection section 106 inside the casing 102 or the casing 104. However, configuration may be made with an imaging complete button provided to the electronic cassette 100, such that when this button is pressed the cassette controller 128 controls to automatically take-up the radiation detection section 106 in the casing 102 or the casing 104 until the accommodated state is reached.

A detachable cooling member is also preferably provided inside the take-up section 108 or the take-up section 110. Providing the cooling member inside the take-up section 108 or the take-up section 110 enables heat transmission to the radiation detection section 106 taken up on the take-up section 108 or the take-up section 110 or heat generation from the radiation detection section 106 to be prevented. The amount of noise incorporated in radiographic images increases when imaging is performed with the radiation detection section 106 maintained at a higher temperature than normal. In particular when the radiation detection section 106 is in a state wound up with a number of layers, as in the present exemplary embodiment, it is advantageous to provide the cooling member inside the take-up section 108 or the take-up section 110 since heat is transmitted across a wide range of the radiation detection section 106. A circular column shaped member concentric to the rotation shaft 112 may, for example, be provided as the cooling member.

Preferably an acceleration sensor and an alarm are provided inside the casing 102 or the casing 104. When the casing 102 or the casing 104 is moved during take-up or feed-out of the radiation detection section 106, this sometimes results in winding the radiation detection section 106 in the wrong direction or in the radiation detection section 106 being damaged. An acceleration sensor is therefore provided in the casing 102 or the casing 104. Preferably the alarm sounds and notifies a user when, based on detection results from the acceleration sensor, the cassette controller 128 detects that the casing 102 or the casing 104 has moved in the other direction to the take-up or feed-out direction of the radiation detection section 106 when the casing 102 or the casing 104 is moving while the radiation detection section 106 is being taken up or fed out. In such cases the cassette controller 128 at the same time preferably also stops take-up or feed-out of the radiation detection section 106. The cassette controller 128 stopping the take-up or feed-out of the radiation detection section 106 enables winding of the radiation detection section 106 in the wrong direction to be prevented.

Note that in the present exemplary embodiment the input section 136 and the display section 142 are provided to the casing 102, however the input section 136 and the display section 142 may be provided to the casing 104. Configuration may alternatively be made such that the input section 136 is a remote controller that is separate to the casings.

Note that while the imaging surface area storage section 138 is provided inside the casing, the imaging surface area storage section 138 may be configured as a detachable external memory. Configuring the imaging surface area storage section 138 as an external memory enables it to be replaced with another having other values for the values of the exposure surface area associated with imaging sites stored in the imaging surface area storage section 138. Another possible manner of use is to exchange the imaging surface area storage section 138 for each patient. The image storage section 137 may also be similarly configured as a detachable external memory. When the image storage section 137 is configured as an external memory, a situation in which one person's radiographic images become mixed in with another's can be avoided by for example exchanging the memory each time imaging is performed.

A handle may be provided to the casing 102 or the casing 104. Providing a handle enables a user to grip the handle to carry the electronic cassette 100 when the radiation detection section 106 is in the accommodated state.

Note that while in the present exemplary embodiment the power to the electronic cassette 100 is switched ON by switching ON the power with a power button 187, the method of switching the power ON is not limited thereto. For example, control may be made such that power is switched ON when a user pulls the casing 102 or the casing 104 and the radiation detection section is externally exposed. Similarly, control may be made such that power is automatically switched OFF when a user manually takes up the radiation detection section 106 and the accommodated state is achieved. For example, configuration may be made such that the take-up amount detection sensor is always conducting, and the power is switched ON when the exposure surface area stops being 0, and the power is switched OFF when the exposure surface area becomes 0. Another conceivable configuration is one in which an acceleration sensor is provided to the take-up section 108 or the take-up section 110 and the control is made such that power is switched ON when, based on detection results of the acceleration sensor, it is detected that the take-up section 108 or the take-up section 110 has rotated.

Preferably an interface is provided capable of detachable connection to mains power, enabling recharging of the battery when the power source is connected to mains power. The electronic cassette 100 may also be driven by power from the power source when mains power is being employed.

Configuration may be made with control such that the power cannot be switched ON and the casing 102 and the casing 104 cannot be separated when the electronic cassette 100 is not in a state capable of imaging. More specifically, control is made such that the power cannot be switched ON and the casing 102 and the casing 104 cannot be separated when the battery 146 is insufficiently charged, when power becomes insufficient during use, or when the temperature of the radiation detection section 106 is higher than an allowable range. A known structure can be employed for the structure that stops the casing 102 and the casing 104 from separating. This is realizable, for example, by providing a stopper that maintains the casing 102 and the casing 104 in contact with each other, and electrically controlling the stopper.

In addition to the take-up section 108 and the take-up section 110, a separate mechanism to perform take-up and feed-out of the radiation detection section 106 may also be provided in the vicinity of the opening portion 116 and the opening portion 118. When the take-up section 108 and the take-up section 110 are rotated in the radiation detection section 106 feed-out direction, the radiation detection section 106 sometimes becomes slack in the casing 102 or the casing 104. By providing a mechanism to take-up or feed-out the radiation detection section 106 in the vicinity of the opening portion 116 or the opening portion 118, the radiation detection section 106 can be externally exposed without slack in the casing 102 or the casing 104.

In the present exemplary embodiment the radiation detection section 106 is a rectangular shape, however there is no limitation of the shape of the radiation detection section 106 to a rectangular shape as long as there is sufficient surface area to enable plural times of radiographic imaging. The radiation detection section 106 may be any shape as long as it can be connected to the rotation shaft 112 and the rotation shaft 114 and is storable inside the casing 102 and the casing 104. For example, the radiation detection section 106 may be formed as a trapezoid long in the vertical direction, the upper base of the trapezoid connected to the rotation shaft 112, and the lower base of the trapezoid connected to the rotation shaft 114. In such a configuration the length of the radiation detection section 106 in a direction perpendicular to the take-up direction of the radiation detection section 106 can be made to change according to take-up on the take-up sections. It thereby becomes possible to change the length of the radiation detection section 106 in a direction perpendicular to the take-up direction in addition to changing the length of the radiation detection section 106 in the take-up direction. The shape of the radiation detection section 106 is also not limited to a regular rectangular shape or trapezoid shape, and configuration may be made with a more complicated shape. For example a shape conforming to the patient body may be employed. Preferably the shape of the radiation detection section 106 is stored in advance in one the storage sections when the shape of the radiation detection section 106 can be changed. By storing the shape of the radiation detection section 106 in advance, the display section 142 can display the shape of the radiation detection section 106 based on the stored shape of the radiation detection section 106. A user can then select the desired imaging region based on the shape of the radiation detection section 106 displayed by the display section 142. Adopting such a configuration enables a user to easily search for and use the desired shape even when using a radiation detection section 106 with more complicated shapes.

The radiation detection section 106 is preferably detachable from the rotation shaft 112 or the rotation shaft 114. When the radiation detection section 106 is detachable then it is possible to remove the radiation detection section 106 from the rotation shaft when it is desired to inserting the radiation detection section 106 under a prone patient 210, as shown in FIG. 7. It is then possible to connect to the casing after inserting only the detached side under the patient 210. Imaging is thereby enabled without imposing burden on the prone patient 210 by lifting the body of the patient 210 more than is necessary. The radiation detection section 106 can be replaced when the radiation detection section 106 has deteriorated overall if the radiation detection section 106 is configured detachable from both the rotation shaft 112 and the rotation shaft 114. Adopting such a configuration enables portions of the electronic cassette 100 other than the radiation detection section 106 to be reused, and means that it is unnecessary to purchase a whole new electronic cassette 100 when the radiation detection section 106 has deteriorated overall. When it is desired to change the shape or characteristics of the radiation detection section 106, this can also be accommodated by exchanging the radiation detection section 106. For example, by additionally purchasing a radiation detection section 106 with a different shape, an electronic cassette can be configured with various shapes of radiation detection sections by swapping over the radiation detection section 106 according to the target use. The electronic cassette 100 preferably automatically reads data from a newly connected radiation detection section 106 when radiation detection sections 106 are swapped over. For example, configuration may be made such that an IC tag is incorporated into the radiation detection section 106, to perform communication with the electronic cassette 100 so as to read the usage status of the newly connected radiation detection section 106 and the shape of the radiation detection section 106.

Preferably casters are attached to the bottom faces of the casings when the radiation detection section 106 is placed in the accommodated state automatically. Providing casters on the bottom face of the casings results in the casing 102 and the casing 104 approaching each other automatically in the radiation detection section 106 storage operation. There is accordingly no need for the user to personally pick up the casings to achieve the radiation detection section 106 accommodated state.

Second Exemplary Embodiment

Figure 12:
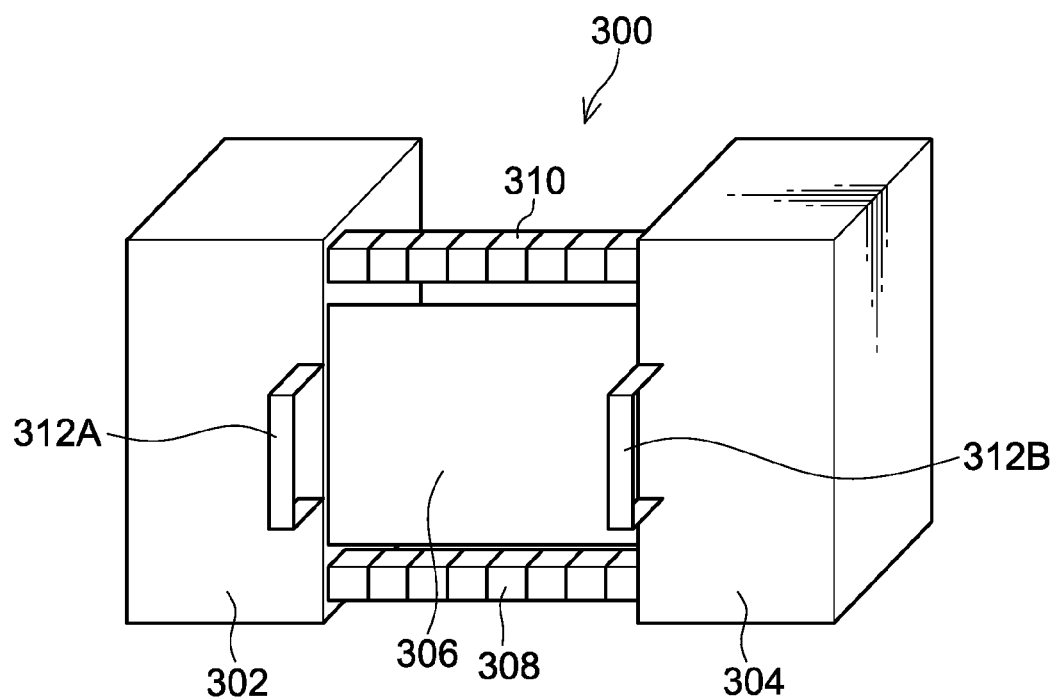
FIG. 12 is a perspective view of an electronic cassette according to a second exemplary embodiment.

FIG. 12 is an external perspective view of an electronic cassette 300 according to the present exemplary embodiment. The external appearance of the electronic cassette 300 differs from that in the first exemplary embodiment in that a support rod 308 and a support rod 310 capable of extending and retracting are provided at an upper portion and a lower portion of a radiation detection section 306, running parallel to the take-up and feed-out direction of the radiation detection section 306. It also differs therefrom in that a handle 312A is provided to the external face of a casing 302 and a handle 312B is provided to an external face of a casing 304.

Figure 13:
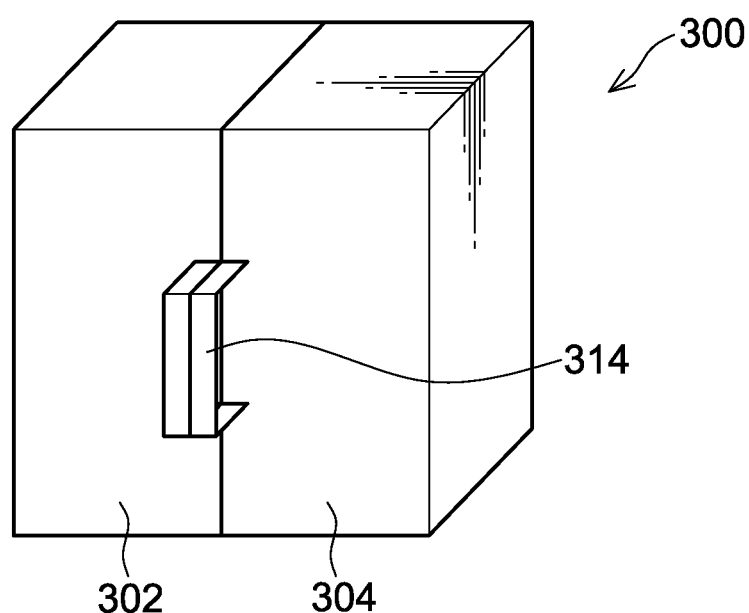
FIG. 13 is a drawing of an electronic cassette according to the second exemplary embodiment in an accommodated state.

FIG. 13 is an external perspective view of a case in which the electronic cassette 300 according to the present exemplary embodiment has the radiation detection section 306 in a accommodated state. When the electronic cassette 300 is in a accommodated state, the casing 302 and the casing 304 are in close contact with each other, and the handle 312A and the handle 312B are in close contact with each other configuring a single handle 314. The electronic cassette 300 is easily transported by the handle 314 when the electronic cassette 300 is in the accommodated state.

FIG. 14 is an external perspective view of the electronic cassette 300. Portions similar to those of the first exemplary embodiment will not be explained. In the present exemplary embodiment, a motor inside the casing 302 extends and retracts the support rod 308 and the support rod 310 in addition to the take-up sections. Specifically, the motor drives extension and retraction of the support rod 308 and the support rod 310 so as to adjust the length of the support rod 308 and the support rod 310 according to changes to the exposure surface area. More specifically, the support rod 308 and the support rod 310 extend to a state in which the radiation detection section 306 is taut. For example, in order to widen the exposure surface area of the radiation detection section 306 a take-up section 316 and a take-up section 318 are rotated by motors, however a slack state of the radiation detection section 306 results when only one of the take-up sections is rotated in a feed-out operation. In such cases, by extending the support rod 308 and the support rod 310 the radiation detection section 306 becomes taut without slackness. When a taut state of the radiation detection section 306 has been achieved an extension/retraction stopper is actuated on the support rod 308 or the support rod 310, disabling further extension or retraction. The stopper is switched OFF with a change in the exposure position of the radiation detection section 306. The stability of the electronic cassette 300 is increased when the casing 302 and the casing 304 are separated from each other by the support rod 308 or the support rod 310 extending or retracting in this manner with changes in the exposure surface area of the radiation detection section 306. Note that control of other portions is similar to that of the first exemplary embodiment and explanation thereof is omitted.

Figure 15A:
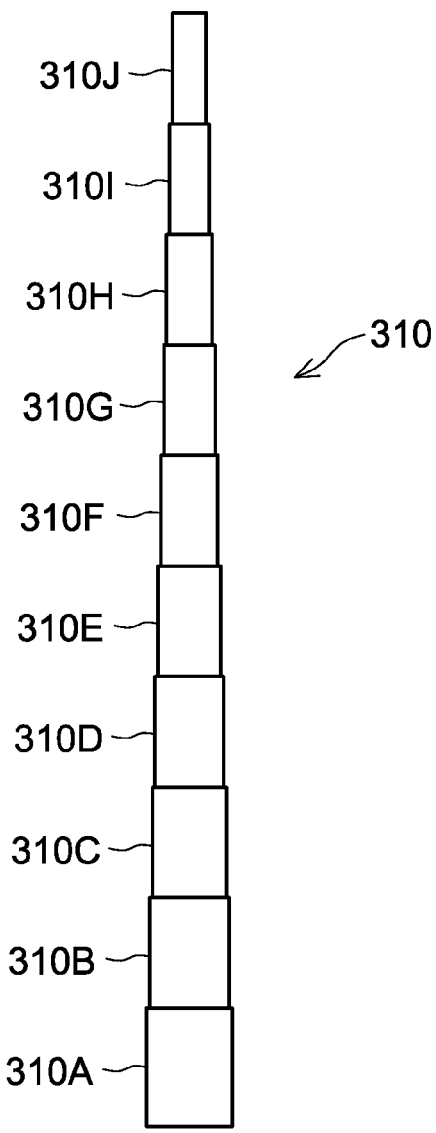
FIG. 15A is a drawing illustrating a structure of a support rod.
Figure 15B:
FIG. 15B is a drawing illustrating a structure of a support rod.

FIG. 15A is a schematic diagram of the support rod 310. A specific structure of the support rod 310 will be explained with reference to FIG. 15A. The support rod 310 is formed by connecting together plural circular cylinder shaped members each having different respective radii and having a radius at the top face that is smaller than the radius at the bottom face. A circular cylinder shaped member 310A has the largest radius and is disposed outermost, the circular cylinder shaped member 310B has a slightly smaller radius than the circular cylinder shaped member 310A, and overlaps at the inside of the circular cylinder shaped member 310A. A circular cylinder shaped member 310C has a radius smaller than that of the circular cylinder shaped member 310B, and overlaps at the inside of the circular cylinder shaped member 310B. The support rod 310 is configured by overlapping circular cylinder shaped members of slightly smaller radii in sequence at the inside. By adopting such a structure, the support rod 310 becomes the length of a single circular cylinder shaped member when refracted, as shown in FIG. 15B, and extends to a length an integer number of times the length of a circular cylinder shaped member when extended. The support rod 308 and the support rod 310 have similar structures to each other. Preferably the support rod 308 and the support rod 310 are provided with a certain amount of rigidity so that they do not bend in the extended state.

Figure 16:
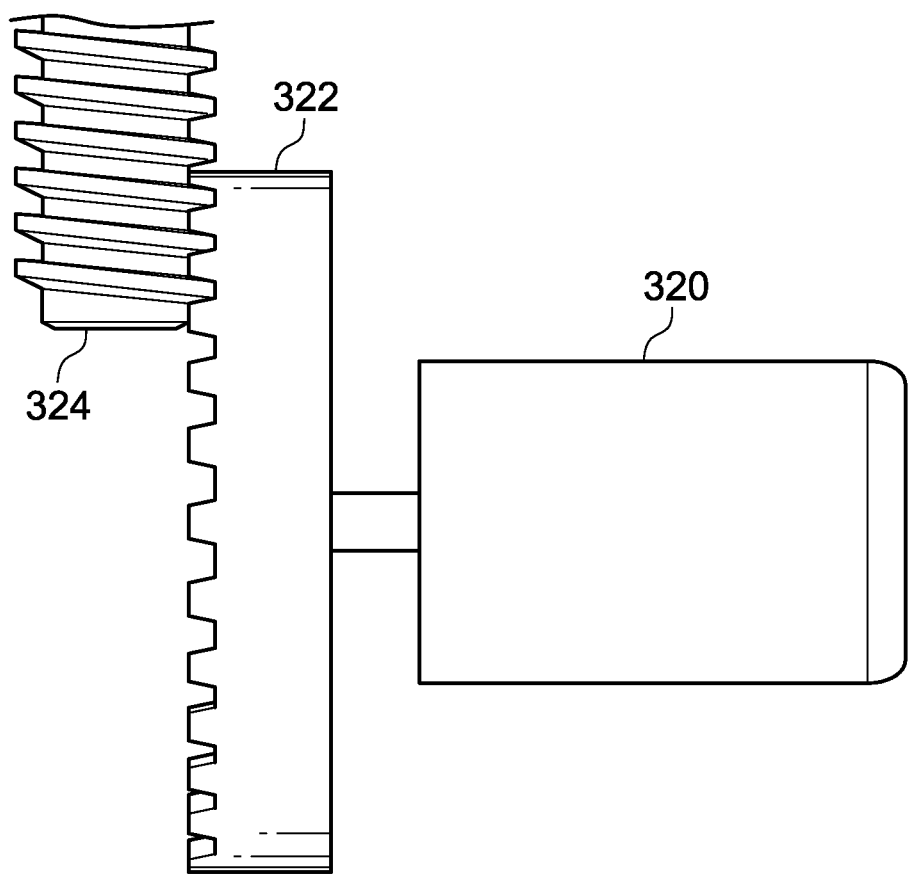
FIG. 16 is a drawing of a structure for a motor to drive a support rod.

The circular cylinder shaped members are driven and extended and retracted by a motor 320. A known structure can be employed for extension and retraction driving with a motor. For example, a structure may be employed in which rotational driving of the motor 320 is converted into up-down movement of a rod 324 through a gear 322, as shown in FIG. 16. The support rod 308 or the support rod 310 can then be extended or refracted by up-down movement of the rod 324 by housing the rod 324 inside the support rod 308 or the support rod 310 and connecting to the rod 324 to the support rod 308 or the support rod 310.

According to the electronic cassette 300 of the present exemplary embodiment as explained above, imaging can be performed without slackness in the radiation detection section 306 due to the structure in which the support rod 308 and the support rod 310 are extended and retracted according to changes in the exposure surface area of the radiation detection section 306. The unstable state in which the casing 302 and the casing 304 are only connected by the radiation detection section 306 can be eliminated by providing the support rod 308 and the support rod 310, thereby raising the overall rigidity of the apparatus. In particular, when the support rod 308 or the support rod 310 are rigid then one or other of the casing 302 or the casing 304 can be prevented from falling over, and damage due to twisting of the radiation detection section 306 can be prevented. Feed-out to the next region of the radiation detection section 306 to be employed can be performed by switching OFF only the stopper in the casing feeding out the radiation detection section 306 and then extending the support rod 308 and the support rod 310. In such cases, unused regions may be wound up by motor, or wound up manually. Power consumption of the motor during feed-out of the radiation detection section 306 can thereby be reduced.

A cable or the like can be passed through the support rod 308 and the support rod 310 due to their hollowness. For example, configuration may be made such that a battery is only provided to the casing 302, and power from this battery is supplied to electrical circuits in the casing 304 by passing a power supply line from the battery through the support rod 308 or the support rod 310. Adopting such a configuration enables noise to be reduced since the power supply line does not pass through the radiation detection section 306 and so it does not adversely affect the pixels of the radiation detection section 306.

Note that a structure of a support rod is not limited to that explained, and any structure may be adopted so long as it is capable of extension and retraction. For example an accordion structure may be employed.

According to the present invention as described above, the exposure surface area and the exposure position of the radiation detection section can be made variable due to the configuration in which the radiation detection section is storable in both the two casings. An electronic cassette can accordingly be provided in which deterioration of a radiation detection section is not concentrated on a single region and no extreme difference in image quality occurs within a single sheet radiation detection section.

The electronic cassette is also provided with an automatic drive mechanism that automatically performs take-up into the casing or feed-out from the casing of the radiation detection section, and performs control to store the usage status of the radiation detection section, and to expose a region that differs from the region of the radiation detection section employed immediately previously. Repeated use of the same region of the radiation detection section is thereby eliminated, and deterioration of the radiation detection section can be distributed.

The electronic cassette also stores the usage status of each region of the radiation detection section, and performs imaging employing the lowest used region of the radiation detection section. Evening out of the usage status of the radiation detection section can accordingly be achieved, and an evening out of the deterioration state of the radiation detection section can be achieved.

Japanese Patent Application Nos. 2010-84581 and 2010-258225 are incorporated in the present specification in their entirety by reference herein.

All cited documents, patent applications and technical standards mentioned in the present specification are incorporated by reference in the present specification to the same extent as if the cited documents, patent applications and technical standards were specifically and individually incorporated by reference in the present specification.

INDUSTRIAL APPLICABILITY

The present invention can be applied to a radiographic imaging device.

The invention claimed is:

1. A radiographic imaging device, comprising:
a flexible radiation detection section that is formed with pixels arrayed in a two dimensional matrix and that detects radiation and converts the detected radiation to radiographic image data;
a first casing;
a second casing;
a first drive mechanism that at least one of accommodates the radiation detection section inside the first casing or feeds out the radiation detection section from inside the first casing; and
a second drive mechanism that at least one of accommodates the radiation detection section inside the second casing or feeds out the radiation detection section from inside the second casing, wherein
a portion at a first end of the radiation detection section is attached to the first drive mechanism, and
a portion at a second end of the radiation detection section is attached to the second drive mechanism.

2. The radiographic imaging device of claim 1, further comprising:
an automatic drive mechanism and a controller that are provided at at least one of the first casing or the second casing;
wherein the automatic drive mechanism automatically drives at least one of the first drive mechanism or the second drive mechanism; and
the controller controls the automatic drive mechanism.

3. The radiographic imaging device of claim 2, further comprising:
a position detection section that detects at least one of the position of the first casing or the position of the second casing with respect to the radiation detection section.

4. The radiographic imaging device of claim 2, wherein:
the radiographic imaging device further comprises a storage section that is provided at at least one of the first casing or the second casing and that stores a usage status of the radiation detection section; and
the controller effects control
so as to identify a region of the radiation detection section that has been employed for imaging based on a detection result of the position detection section, and
so as to store the identified region of the radiation detection section in the storage section as the radiation detection section usage status.

5. The radiographic imaging device of claim 4, wherein the controller:
stores the usage status of the radiation detection section by storing the region of the radiation detection section that is employed for imaging in the storage section every time imaging is performed; and
controls the automatic drive mechanism so as to externally expose a region of the radiation detection section different to the region of the radiation detection section that was employed for imaging immediately previously.

6. The radiographic imaging device of claim 5, wherein the controller controls the automatic drive mechanism based on the usage status of the radiation detection section stored in the storage section such that the usage status of each region of the radiation detection section becomes substantially equivalent.

7. The radiographic imaging device of claim 6, wherein the controller controls the automatic drive mechanism every time imaging is performed such that:
the radiation detection section is fed out from the first casing or the second casing in order to use a region of the radiation detection section; and
when there is insufficient region of the radiation detection section for use in the feed-out direction, controls the automatic drive mechanism to use a region of the radiation detection section in the opposite direction to the feed-out direction from an end portion of the radiation detection section.

8. The radiographic imaging device of claim 7, wherein:
the controller is capable of changing the region of the radiation detection section to be exposed when the number of times of use of the radiation detection section stored in the storage section exceeds a predetermined number of times.

9. The radiographic imaging device of claim 8, wherein:
the radiographic imaging device further comprises a cumulative radiation detection function that detects a cumulative radiation dose of the radiation detection section; and
the controller is capable of changing the region of the radiation detection section to be exposed when the cumulative radiation dose detected by the cumulative radiation dose detection function exceeds a preset threshold value.

10. The radiographic imaging device of claim 5, wherein the controller effects control so as to store, in the storage section, a usage status for each region of the radiation detection section, each region having been partitioned at a specific interval.

11. The radiographic imaging device of claim 10, wherein the controller controls the automatic drive mechanism so as to externally expose a region of the radiation detection section with the lowest usage status based on the usage status stored in the storage section for each region of the radiation detection section that has been partitioned at the specific interval.

12. The radiographic imaging device of claim 5, wherein:
the radiographic imaging device further comprises an input section provided at at least one of the first casing or the second casing;
the storage section stores a plurality of types of imaging surface area; and
the input section sets one imaging surface area from out of the plurality of types of imaging surface area stored in the storage section.

13. The radiographic imaging device of claim 12, wherein the controller:
identifies a surface area of a region of the radiation detection section that is being externally exposed based on a detection result of the position detection section; and
controls the automatic drive mechanism such that the surface area of the region of the radiation detection section that is being externally exposed is substantially the same as the imaging surface area set by the input section.

14. The radiographic imaging device of claim 3, wherein:
the position detection section detects the position of the first casing or the second casing with respect to the radiation detection section based on the surface area of a region of the radiation detection section currently stored in the first casing, based on the surface area of a region of the radiation detection section currently stored in the second casing and based on the surface area of the entire region of the radiation detection section.

15. The radiographic imaging device of claim 4, wherein:
the controller associates radiographic image data obtained by radiographic imaging with a region of the radiation detection section that was employed for the radiographic imaging, as identified based on a detection result of the position detection section, and saves the radiographic image data in the storage section.

16. The radiographic imaging device of claim 1, wherein:
the first drive mechanism comprises a first take-up section rotatably provided inside the first casing; and
the second drive mechanism comprises a second take-up section rotatably provided inside the second casing.

17. The radiographic imaging device of claim 16, wherein:
the radiation detection section is wound inside the first casing or the second casing by a take-up operation in which the first take-up section or the second take-up section rolls the radiation detection section in a take-up direction; and
the radiation detection section that has been taken up on the first take-up shaft or the second take-up shaft is fed out from the first casing or the second casing by a feed-out operation in which the radiation detection section is pulled in a feed-out direction from inside the first casing or the second casing.

18. The radiographic imaging device of claim 1, further comprising a display section provided at at least one of the first casing or the second casing.

19. The radiographic imaging device of claim 1, further comprising a stopper that is provided at at least one of the first casing or the second casing and that controls whether or not take-up or feed-out of the radiation detection section can be performed.

20. The radiographic imaging device of claim 2, wherein at least one of the first drive mechanism or the second drive mechanism has a hollow structure and the controller is housed in the hollow structure.

21. The radiographic imaging device of claim 1, further comprising a cooling member detachably provided at the hollow structure.

22. The radiographic imaging device of claim 1, wherein:
the first casing comprises a first holder section;
the second casing comprises a second holder section; and
the first holder section and the second holder section are superimposed one on the other to configure a single holder section when the first casing and the second casing are superimposed one on the other.

23. The radiographic imaging device of claim 3, wherein:
the first casing or the second casing further comprises an acceleration sensor; and
the radiographic imaging device further comprises an alarm section that, in a situation in which the first casing or the second casing is being detected by the position detection section as changing position in the radiation detection section storage direction or changing position in the radiation detection section feed-out direction, the alarm section detects that the first casing or the second casing has moved in a different direction to the radiation detection section storage direction or take-up direction based on a detection result of the acceleration sensor.

24. The radiographic imaging device of claim 2, further comprising a battery detachably provided at at least one of the first casing or the second casing.

25. The radiographic imaging device of claim 1, wherein the radiation detection section is formed with stacked layers comprising a scintillator configured to include columnar crystals of a phosphor that emits light upon irradiation with radiation, and solid state detection elements that convert light emitted by the scintillator into charges and accumulate the charges.

26. The radiographic imaging device of claim 25, wherein the phosphor is CsI.

27. The radiographic imaging device of claim 25, wherein the radiation detection section is stored by taking up such that the solid state detection elements are on the inside, and the radiation detection section includes partings that are provided at specific intervals in the scintillator and that run in a direction orthogonal to the take-up direction.

28. The radiographic imaging device of claim 25, wherein:
the solid state detection elements are formed using an organic photoelectric conversion material; and
the radiation detection section is formed with an active layer comprising an amorphous oxide material, an organic semiconductor material or carbon nanotubes, and is formed with thin film transistors that read charges from the solid state detection elements.

* * * * *